(12) United States Patent
Lakowicz et al.

(10) Patent No.: US 6,197,534 B1
(45) Date of Patent: Mar. 6, 2001

(54) ENGINEERED PROTEINS FOR ANALYTE SENSING

(76) Inventors: Joseph R. Lakowicz, 10037 Fox Den Rd., Ellicott City, MD (US) 21042; Leah Tolosa, 500 Johnnycake Rd., Baltimore, MD (US) 21244; Lisa Eichhorn, 1708 Peachwood Ct., Finksburg, MD (US) 21048; Govind Rao, 10401 Northdale Rd., Columbia, MD (US) 21044

(*) Notice: Subject to any disclaimer, the term of this patent is extended or adjusted under 35 U.S.C. 154(b) by 0 days.

(21) Appl. No.: 09/354,106

(22) Filed: Jul. 15, 1999

Related U.S. Application Data
(60) Provisional application No. 60/093,188, filed on Jul. 17, 1998, and provisional application No. 60/104,237, filed on Oct. 14, 1998.

(51) Int. Cl.[7] .............................. C12Q 1/54; C12Q 1/37; C07H 1/00; C13K 5/00
(52) U.S. Cl. ............................... 435/14; 435/23; 435/25; 435/968; 536/1.11; 536/123.13; 536/123.1
(58) Field of Search .................................. 435/14, 23, 25, 435/968; 536/1.11, 123.13, 123.1

(56) References Cited

PUBLICATIONS

Lakowicz et al, J. Biomed. Opt., vol. 4(4), p443–449, 1999.*
Jacques et al., Controlled removal of human stratum corneum by pulsed laser. *The Journal of Investigative Dermatology*, 88(1) (1987) 88–93.
Rabinovitch et al., Noninvasive glucose monitoring of the aqueous humor of the eye: Part 1. Measurement of very small optical rotations. *Diabetes Care* 5(3) (1982) 254–258.
Castellano et al., A water–soluble luminescence oxygen sensor. *Photochemistry and Photobiology*, 67(2) (1998), 179–183.
Feddersen et al., Digital parallel acquisition in frequency domain fluorimetry. *Rev. Sci. Instrum.*, 60 (9) (1989), 2929–2936.
Lakowicz et al., Optical sensing of glucose using phase–modulation fluorimetry. *Analytica Chimica Acta*, 271 (1993) 155–164.
Sipior et al., Single quantum well light emitting diodes demonstrated as excitation sources for nanosecond phase–modulation fluorescence lifetime measurements. *Rev. Sci. Instrum.* 67(11), (1996), 3795–3798.
Berndt et al., Phase–modulation fluorometry using a frequency–doubled pulsed laser diode light source. *Rev. Sci. Instrum.*, 61(7) (1990), 1816–1820.
Berndt et al., Electroluminescent lamp–based phase fluorometer and oxygen sensor. *Analytical Biochemistry*, 201 (1992), 319–325.
Sipior et al., Blue light–emitting diode demonstrated as an ultraviolet excitation source *for nanosecond phase–modulation fluorescence lifetime measurements. Rev. Sci. Instrum.*, 68(7) (1997), 2666–2670.
Tolosa et al., Optical assay for glucose based on the luminescence decay time of the long wavelength dye Cy5™. *Sensors and Actuators*, B45 (1997) 93–99.
Tamada et al., Measurement of glucose in diabetic subjects using noninvasive transdermal extraction. *Nature Medicine* 1(11) (1995), 1198–1201.
Scholle et al., Sequence of the *mg1B* gene from *Escherichia coli* K12: Comparison of wild–type and mutant galactose chemoreceptors. *Mol. Gen. Genet* 208 (1987) 247–253.

(List continued on next page.)

*Primary Examiner*—Louise N. Leary
(74) *Attorney, Agent, or Firm*—Rothwell, Figg, Ernst & Manbeck

(57) ABSTRACT

Disclosed are methods and sensors for detecting the presence or concentration of an analyte in a sample, preferably a sugar such as glucose, which preferably utilizes a labeled engineered protein, or fragment thereof, that is capable of binding the analyte to be detected.

58 Claims, 23 Drawing Sheets

PUBLICATIONS

Lakowicz et al., Low–frequency modulation senors using nanosecond fluorophores. *Anal. Chem.* 70 (1998) 5115–5121.

Tolosa et al., Lifetime–based sensing of glucose using energy transfer with a long lifetime donor. *Analytical Biochemistry* 250 (1997), 102–108.

Robinson et al, Noninvasive glucose monitoring in diabetic patients: A preliminary evaluation. *Clin. Chem.*, 38/9 (1992) 1618–1622.

Heise et al., Noninvasive blood glucose sensors based on near–infrared spectroscopy. *Artif. Organs*, 18(6) (1994), 439–447.

Burmeister et al., Phantoms for noninvasive blood glucose sensing with near infrared transmission spectroscopy. *Photochemistry and Photobiology*, 67(1) (1998), 50–55.

March et al., Ocular glucose sensor. *Trans. Am. Soc. Artif Intern. Organs*, 28 (1982), 232–235.

Meadows et al., Fiber–optic biosensors based on fluorescence energy transfer. *Talanta*, 35(2) (1998) 145–150.

Schultz et al., Affinity sensor: A new technique for developing implantable sensors for glucose and other metabolites. *Diabetes Care* 5(3) (1982) 245–253.

Schultz et al., Affinity sensors for individual metabolites. *Biotechnology and Bioengineering Symp.* 9 (1979) 65–71.

Claremont, Biosensors: clinical requirements and scientific promise. *Journal of Medical Engineering and Technology*, 11(2) (1987) 51–56.

Ito et al., Development of a transcutaneous blood–constituent monitoring method using a suction effusion fluid collection technique and an ion–sensitive field–effect transistor glucose sensor. *Medical and Biological Engineering and Computing*, (32) (1994), 242–246.

Claremont et al., Subcutaneous implantation of a ferrocene–mediated glucose sensor in pigs. *Diabetologia* 29(1986), 817–821.

Yokoyama, Integrated biosensor for glucose and galactose. *Analytica Chimica Acta*, 218 (1989) 137–142.

Boos et al., Transport properties of the galactose–binding protein of *Escherichia coli*. *Journal of Biological Chemistry*, 247(3) (1972), 917–924.

Boos, Structurally defective galactose–binding protein isolated from a mutant negative in the β–methylgalactoside transport system of *Escherichia coli*. *J. Biol.* Chem,; 247(17) (1972), 5414–5424.

Strange et al., Receptor interactions in a signalling system: Competition between ribose receptor and galactose receptor in the chemotaxis response. *Proc. Nat. Acad, Sci, USA*, 73(3) (1976), 762–766.

Careaga et al., Large amplitude twisting motions of an interdomain hinge: A disulfide trapping study of the galactose–glucose binding protein. *Biochemistry*, 34 (1995) 3048–3055.

Schier et al., al., An evaluation and comparison of reflolux II and glucometer II, two new portable reflectance meters for capillary blood glucose determination. *Diabetes Research and Clinical Practice*, 4 (1988) 177–181.

Marvin et al., Engineering biosensors by introducing fluorescent allosteric signal transducers: Construction of a novel glucose sensor. *J. Am. Chem. Soc.*, 120(1) (1998), 7–11.

Marvin et al., The rational design of allosteric interactions in a monomeric protein and its applications to the construction of biosensors. *Proc. Natl. Acad. Sci. USA* 94 (1997), 4366–4371.

Neu et al., The release of enzymes from *Escherichia coli* by osmotic shock and during the formation of spheroplasts. *Journal of Biological Chemistry*, 240(9) (1965), 3685–3691.

Zukin et al., Properties of the galactose binding protein of *salmonella typhimurium* and *Escherichia coli*. *Biochemistry* 16(3) (1977), 381–386.

Harms et al., Low cost phase–modulation measurements of nanosecond fluorescence lifetimes using a lock–in amplifier. *Rev. Sci. Instrum.*, 70(2) (1999), 1535–1539.

Alcala, Comment on "digital parallel acquistion in frequency domain fluorometry". *Rev. Sci. Instrum.*, 62(6) (1991), 1672–1673.

Feddersen et al., Reply to "comment on 'digital parallel acquisition in frequency domain fluorometry'. "*Rev. Sci. Instrum.*, 62(6) (1991), 1674.

\* cited by examiner

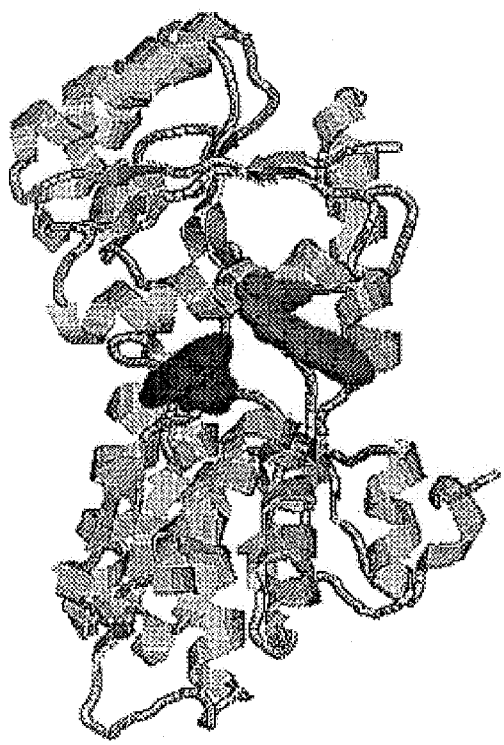 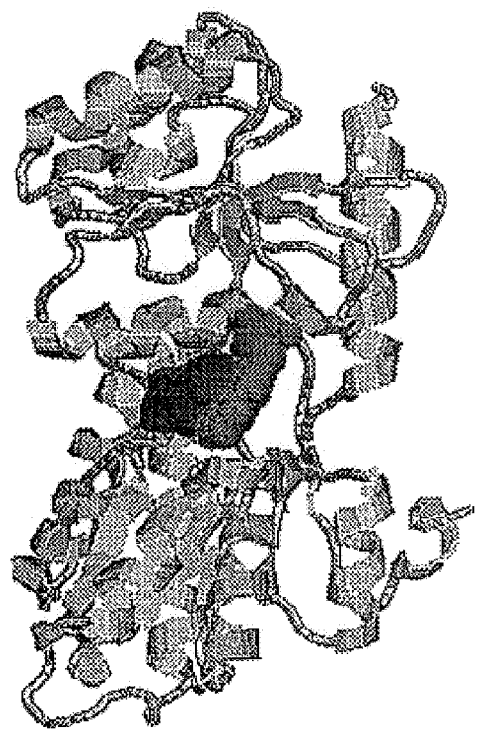
PYRENE AT 182
FIG. 6A
PYRENE AT 26
FIG. 6B

ENGINEERED PROTEINS FOR ANALYTE SENSING

CROSS-REFERENCES TO RELATED APPLICATIONS

This application claims the benefit of application Ser. No. 60/093,188 filed Jul. 17, 1998 and of application Ser. No. 60/104,237 filed Oct. 14, 1998.

STATEMENT REGARDING FEDERALLY SPONSORED RESEARCH OR DEVELOPMENT

The work described herein was supported by National Institutes of Health Grants RR-08119 and 1-RO1-RR10955.

BACKGROUND OF THE INVENTION

1. Field of the Invention

The present invention relates to the determination of the presence or concentration of an analyte, such as a sugar, in a sample, using a labeled protein sensor.

2. Description of the Related Art

A bibliography follows at the end of the Detailed Description of the Invention. The listed references are all incorporated herein by reference.

Diabetes results in long-term health consequences including cardiovascular disease and blindness. These adverse long-term health consequences result from erratic levels of blood glucose in diabetics. To control the long-term complications associated with diabetes, blood glucose levels must be tightly regulated. This requires careful monitoring of blood glucose involving the unpleasant procedure of drawing blood.

The need for real-time measurement of blood glucose has resulted in efforts to develop non-invasive and minimally invasive methods to monitor blood glucose. A wide variety of methods have been proposed, including near infrared spectroscopy [1–3], optical rotation [4, 5], amperometric [6, 7], calorimetric [8, 9] and fluorescence detection [10–15]. In spite of intensive efforts, no method is presently available for non-invasive measurement of blood glucose.

Most glucose sensors that use biological elements for signal transduction use electrochemical or calorimetric detection of glucose oxidase activity. This method is associated with difficulties including the influence of oxygen levels, inhibitors in the blood, and problems with electrodes. In addition, detection results in consumption of the analyte which can cause difficulties when measuring low glucose concentrations. Electrochemical measurements are known to require frequent calibration, which is not acceptable for a continuous glucose monitor.

Using fluorescence, glucose can be measured using fluorophores which respond either to glucose or to proteins such as concanavalin A (ConA). Glucose assays based on proteins are typically competitive assays in which glucose disrupts the binding of ConA to a glucose containing polymer such as dextran. ConA binding to the glucose polymer is typically detected by resonance energy transfer (RET).

While a practical glucose sensor such as ConA-dextran may be used to successfully detect glucose by competitive RET assay, it is not completely reversible [13–15]. ConA and dextran form aggregates which with time become increasingly resistant to disruption by glucose. A sensor is not useful for glucose monitoring unless binding is reversible.

Another approach to developing a biosensor is to genetically engineer a protein for site-specific positioning of allosteric signal transducing molecules. Structural principles are used to take advantage of cooperative interactions between the signaling molecule and ligand binding. This technique has been applied to Maltose binding protein and Glucose/Galactose binding protein of *Escherichia coli* (GGBP) [16, 17]. Structural studies of GGBP reveal two domains, the relative positions of which change upon the binding of glucose [18]. Such conformational changes can be expected to result in spectral changes of environmentally sensitive probes, or changes in the transfer efficiency between donor and acceptor pairs covalently bound to the protein. Spectral changes of environmentally sensitive probes have been reported for GGBP [17].

However, there remains a need in the art for improved methods for determining the presence or concentration of glucose using fluorescent sensing molecules.

SUMMARY OF THE INVENTION

In one aspect, the present invention relates to a method for determining the presence or concentration of an analyte in a sample, comprising the steps of:

a) providing a protein sensing molecule that is capable of binding said analyte in said sample, said molecule having a detectable quality that changes in a concentration-dependent manner when said molecule is bound to said analyte;

b) exposing said sensing molecule to said sample; and c) measuring any change in said detectable quality to thereby determine the presence or concentration of said analyte in said sample.

In another aspect, the present invention provides a sensor for determining the presence or concentration of an analyte in a sample, which comprises:

a) a protein sensing molecule that is capable of binding to the analyte in said sample, said molecule having a detectable quality that changes in a concentration-dependent manner when said molecule is bound to the analyte;

b) a radiation source which is capable of causing said sensing molecule to emit said detectable quality; and c) means for detecting changes in said detectable quality in response to said analyte binding.

BRIEF DESCRIPTION OF THE DRAWINGS

FIG. 6 depicts the energy minimized structure of GBBP labeled with pyrene at residues 26 and 182. In the absence of glucose at 37° C. the pyrene residues appear to be closely stacked (right). In the presence of glucose, the amount of eximer emission decreases, suggesting that the pyrene residues become unstacked and more comparable to the room temperature conformation (left).

DETAILED DESCRIPTION OF THE PREFERRED EMBODIMENTS

Figure 1:
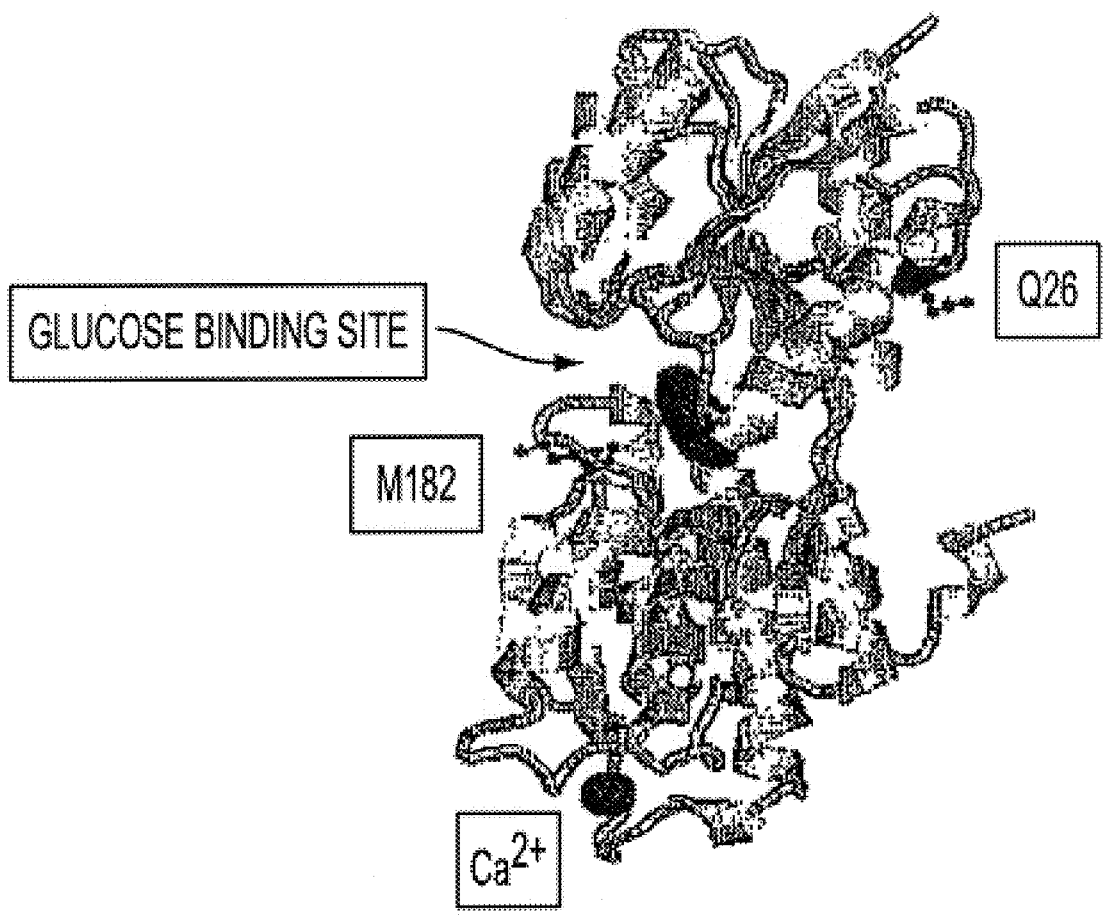
FIG. 1 depicts the three-dimensional crystal structure of the glucose-galactose binding protein (GGBP) showing the locations of residues 26 and 182 in the presence of bound glucose.

The present invention is based on the discovery that certain proteins may be used as sensing molecules to determine the presence or concentration of an analyte in a sample. The analyte includes sugars such as glucose, lactose, galactose, sucrose, maltose, etc., with glucose being most preferred.

The term "protein" as used herein includes not only a full length native protein, but also smaller polypeptide fragments which display the desirable binding characteristics described herein. The protein may be any protein that binds reversibly to the analyte to be detected and which displays a detectable spectral change. Other desirable characteristics include having a single binding site for the analyte, which minimizes aggregation due to cross-linking and maximizes reversibility of the sensor. It is also desirable that the protein be stable and easy to purify following cloning and expression. Also, cooperative binding of the analyte is also desirable, as that effect could increase spectral changes in the physiologically important range of analyte concentrations. It is also preferable that the protein bind the analyte in question without displaying significant chemical transformation of the analyte.

Preferably, the protein is an *E. coli* glucose/galactose binding protein ("GGBP") as previously described [38], or functionally equivalent fragments thereof. As a sensor for glucose monitoring, GGBP has several favorable features including a single glucose binding site and high affinity for glucose; GGBP binds glucose with a dissociation constant near 0.8 $\mu$M. The single site, and lack of polymeric acceptors, results in complete reversibility upon removal of glucose. Like similar transport proteins from other bacteria, GGBP is highly specific for binding glucose and/or galactose. The apparent binding affinity of GGBP for sugars other than glucose or galactose is typically 100–1000 fold weaker [19–22]. The high affinity for glucose also will enable use of the sensor with small volumes of blood or interstitial fluid; a protein sensor with a low affinity could not be used to measure $\mu$M glucose concentrations.

Proteins other than GGBP may be used in the present invention, for example, hexokinase, glucokinase, etc. For use in detecting blood glucose levels, the glucose sensor protein would have to have a lower affinity constant for glucose. This could be accomplished with mutants of hexokinase, for example, which have a lower affinity for glucose, or possibly with mutants of GGBP engineered to have a lower glucose binding constant.

Modified proteins can be suitable sensing molecules. The modification may serve one or more of several purposes. For example, a protein may be modified in order to adjust its binding constant with respect to the analyte; to change the long-term stability of the protein; to conjugate the protein to a polymer; to provide binding sites for detectable labels; etc.

The sensing molecule has a detectable quality that changes in a concentration-dependent manner when the molecule is bound to glucose. In one embodiment, the detectable quality results from a detectable label associated with the sensing molecule. The label may be covalently or non-covalently bound to the sensing molecule. A wide range of suitable labels are known. For example, the label may be a fluorescent label, a non-fluorescent energy transfer acceptor, etc. The label may comprise an energy donor moiety and an energy acceptor moiety, each bound to the sensing molecule and spaced such that there is a detectable change when the sensing molecule is bound to the analyte.

Preferably, the detectable quality is a detectable spectral change. Such includes changes in fluorescent decay time (determined by time domain or frequency domain measurement), fluorescent intensity, fluorescent anisotropy or polarization; a spectral shift of the emission spectrum; a change in time-resolved anisotropy decay (determined by time domain or frequency domain measurement), etc.

Preferably, the detectable quality relates to changes in fluorescence. The sensing molecule may be labeled with one or more detectable labels, and may have engineered therein one or more cysteine residues for assisting in the incorporation of labels. There are many suitable labels or label pairs that would be well-known to one of ordinary skill in the art. Such includes solvent sensitive probes such as the dansyl probes, ananilinonapthanele probes, deproxyl probes, phthalamide probes, amino pH phthalamide probes, and probes comparable to Prodan, Lordan or Acrylodan. Such probes are sensitive to the polarity of the local environment and are well known to those of skill in the art.

Other useful probes include those which display resonance energy transfer (RET). Many such donor-acceptor pairs are known, and include fluorescein to rhodamine, coumarin to fluorescein or rhodamine, etc. Still another class of useful label pairs include fluorophore-quencher pairs in which the second group is a quencher which decreases the fluorescence intensity of the fluorescent group. Some known quenchers include acrylamide groups, heavy atoms such as iodide and bromate, nitroxide spin labels such as TEMPO, etc.

When GGBP is the sensing molecule, it is especially useful to modify the molecule to include cysteine residues at one or both of positions 26 and 182. By genetically engineering mutant GGBP's with selectively placed cysteines, thiol-reactive molecules may be covalently bound to the protein. Sites are selected based on the structure of the protein so that, for example, glucose binding will cause spectral changes for GGBP labeled with environmentally sensitive probes. In some embodiments, the conformational change of GGBP causes interactions between fluorophores bound to separate domains of the protein which move relative to each other in response to glucose binding.

Figures 2A, 2B:
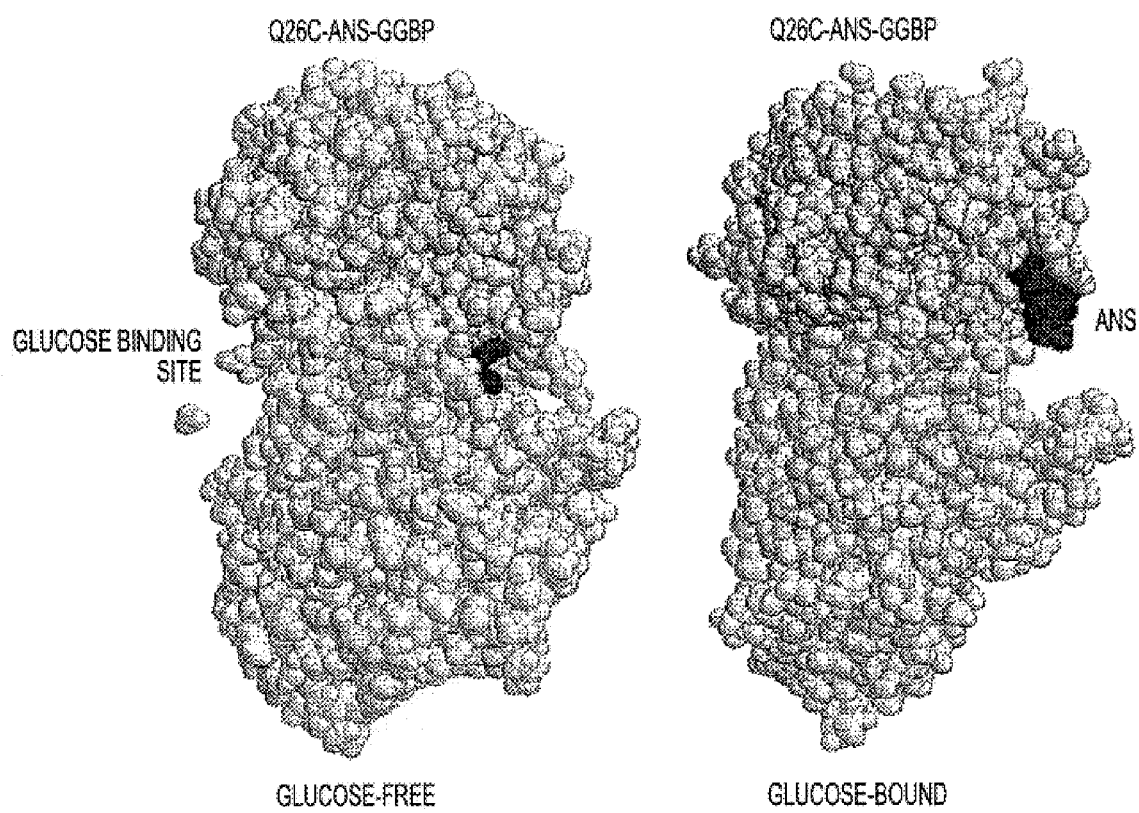
FIG. 2 depicts the structure of Q26C-ANS-GGBP in the absence and presence of glucose. In the presence of glucose, the environmentally sensitive ANS probe is more exposed to the aqueous phase.

Mutant GGBPs are created by replacing one amino acid residue with cysteine at position 26, or replacing two amino acid residues with cysteines at positions 26 and 182 (FIG. 1). These positions are useful because they are close to the hinge region between the two domains of GGBP. Site 26 is exposed by conformational change of the protein upon glucose binding, thereby changing the environment of a probe bound at that site (see FIG. 2).

The mutant GGBPs have one or two cysteine-substituted residues in positions ideal for the covalent attachment of probes such that, when labeled with suitable fluorescent probes, glucose binding causes spectral changes of environmentally sensitive probes or changes in energy transfer efficiency. Additionally, mutant GGBPs may have attached fluorophores with widely spaced lifetimes, permitting modulation-based glucose sensing. This invention also describes GGBP glucose sensors that are fusion proteins with green fluorescent protein which, by changes in energy transfer efficiency on glucose binding, can measure glucose.

In one embodiment of the double-cysteine mutant, GGBP is genetically engineered so that cysteines replace residues at positions 26 and 182 wherein a thiol-reactive donor dye and a thiol-reactive acceptor dye can be covalently bonded to the cysteine residues (see FIG. 1). The cys26 to cys182 distance changes upon glucose binding, moving probes bound at these sites relative to each other (see Example 3).

Figure 3A:
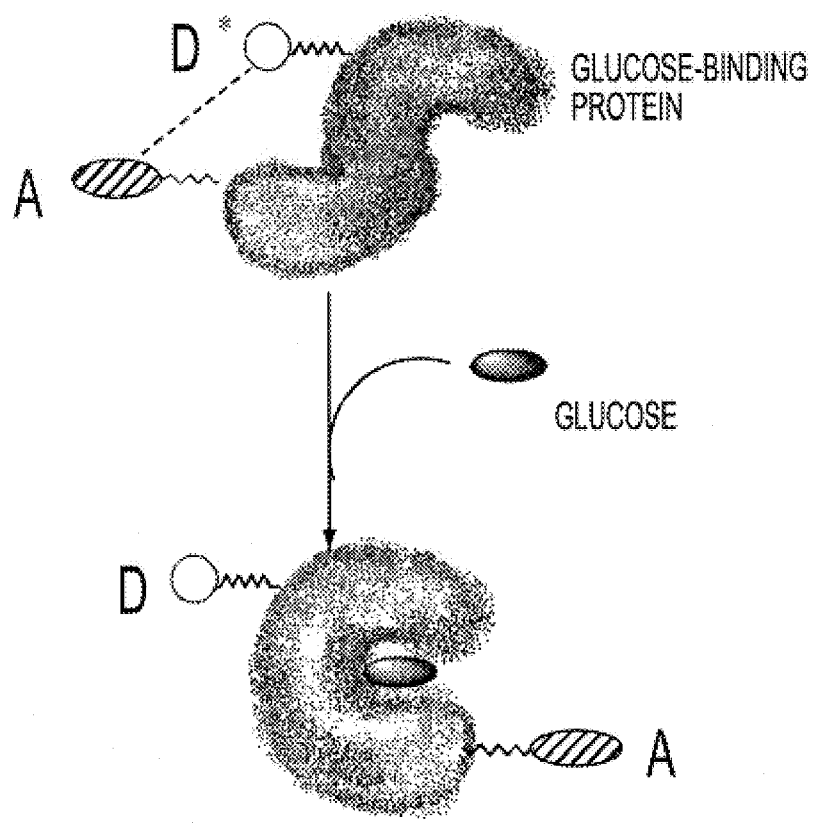
FIG. 3 depicts a hypothetical FRET assay of glucose based on protein conformational changes, wherein donor and acceptor dyes are separated upon glucose binding ($\tau$=lifetime, $\phi$=phase angle).
Figure 3B:
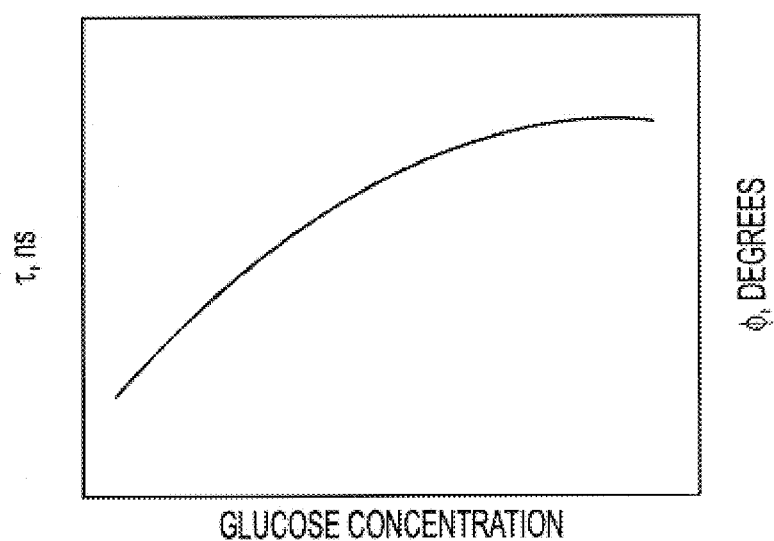
Figure 4A:
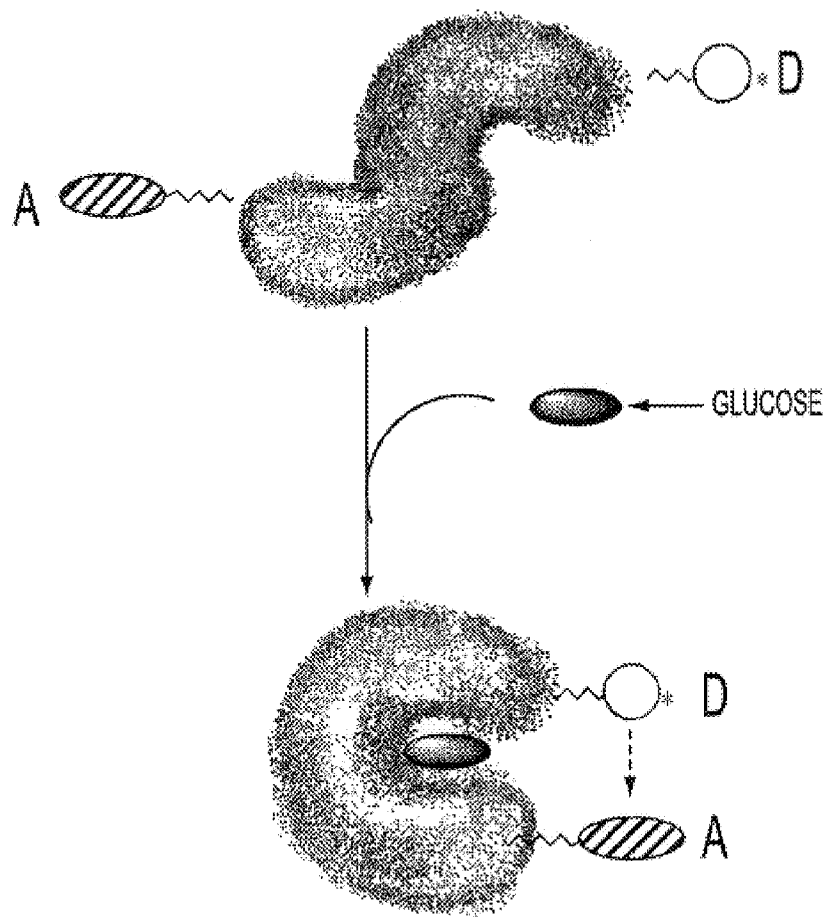
FIG. 4 depicts a hypothetical FRET assay of glucose based on protein conformational changes, wherein donor and acceptor dyes are brought closer together upon glucose binding ($\tau$=lifetime, $\phi$=phase angle).
Figure 4B:
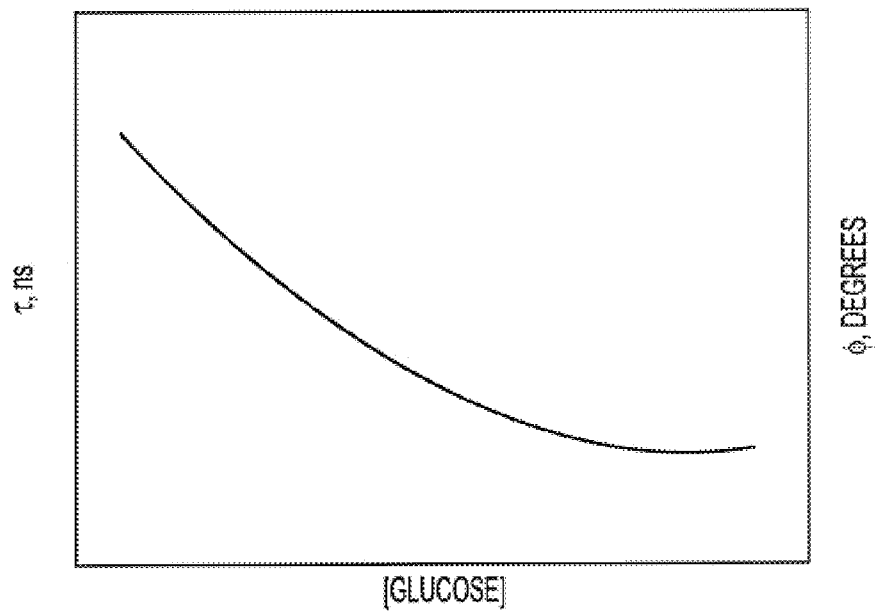

Alternatively, instead of genetically engineering GGBP, donor and acceptor dyes may be attached by making a fusion protein, as described in Example 4. Therefore, for the double cysteine mutant, labeled for example with a donor-acceptor pair, glucose binding causes changes in the transfer efficiency. FIGS. 3 and 4 schematically demonstrate how the conformational changes of GGBP upon glucose binding can shift the relative positions of carefully positioned donor and acceptor molecules.

The glucose sensors of this invention are capable of measuring micromolar glucose concentrations without reagent consumption. Because of their high sensitivity to glucose, mutant GGBP's may be used to measure the low glucose concentrations known to be present in extracted interstitial fluid [23]. Samples from interstitial fluid are known to be painlessly available using methods which perturb the outermost layer of skin, the stratum corneum, for example by laser ablation [24] and weak suction [25].

A glucose sensor or monitor based on GGBP can be expected to display a number of favorable features. The use of a single sensor promises a fast response time, limited by the rate of glucose transport to the protein. This contrasts with the slower response expected for competitive glucose assays in the prior art due to the need for diffusion of two macromolecules, the glucose-binding and the glucose-containing moieties. For a GGBP-based sensor, the only motion needed is of the two domains of the proteins, which should readily occur even in polymeric supports.

When labeled with suitable fluorophores, useful spectral changes are observed for both the single and double cysteine mutants of GGBP. Glucose binding could be detected by changes in emission intensity, anisotropy, lifetime or energy transfer efficiencies. These engineered proteins are expected to be useful for real-time glucose measurements in a variety of convenient formats. Similarly useful spectral shifts may be observed with fluorophore-labeled fusion proteins created from GGBP or its mutants.

Finally, the spectral changes shown for GGBP can presently be measured with low cost devices. Excitation for nanosecond lifetime-based sensing can be accomplished with laser diodes [26], light emitting diodes (LEDs) [27], or electroluminescence light sources [28]. Based on these advances in low-cost fluorescence detection, sensors based on GGBP may be used in hand-held devices for real time monitoring of glucose.

In additional embodiments, a sensor may use a variety of sensing molecules, with different fluorescent labels. Additionally, a sensor may utilize multiple sensing molecules with a range of glucose binding constants. Glucose sensors may be configured using more than one protein, providing accurate measurements over a wide range of glucose concentrations. Engineered glucose-sensitive proteins, coupled with new methods to painlessly extract interstitial fluid, provide an excellent promising near-term method for real-time monitoring of glucose. The methods described herein may be readily extended to other analyte binding proteins, thus paving the way for a new generation of biosensors.

The following examples further illustrate the invention and are not to be construed to limit the claims.

EXAMPLE 1

Construction and Isolation of a Single Cysteine Mutant of GGBP

Figure 5:
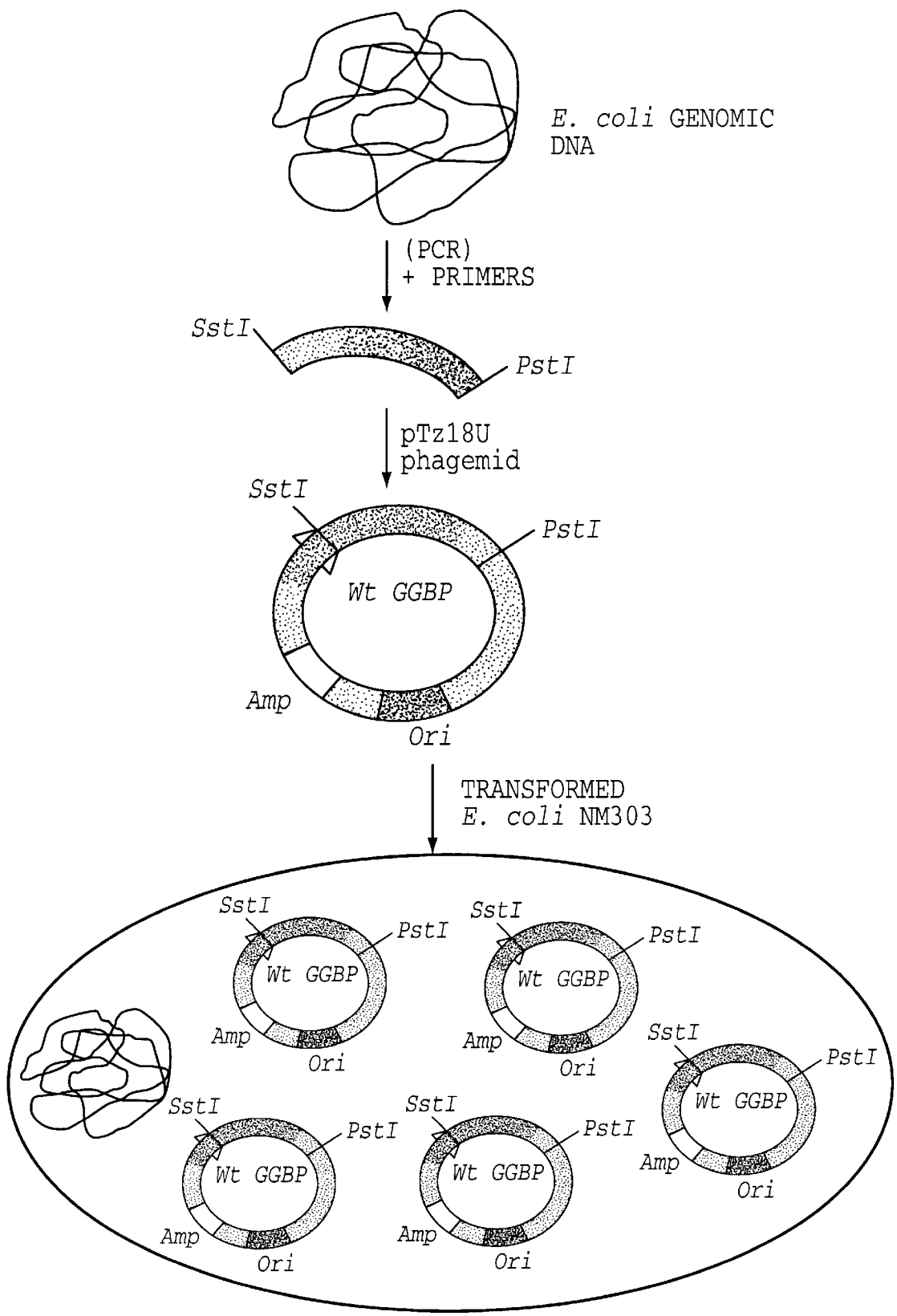
FIG. 5 depicts the cloning of the wild type mglb gene.

One embodiment of the invention comprises a GGBP mutated so that a single cysteine replaces a glutamine residue at position 26 (see FIG. 5). The mglb gene that encodes for wild type GGBP and its natural promoter were isolated from the *E. coli* K-12 genome and amplified by PCR. The gene-promoter fragment was inserted into the PstI/SstI restriction sites of the pTz18U phagemid (Bio Rad Laboratories). The resulting plasmid, pJL01 was used as template for the construction of the Q26C mutant. Site-directed mutagenesis was accomplished using the Quick-Change™ mutagenesis kit from Stratagene. The DNA sequencing data verified the presence of the desired point mutation.

The mono-cysteine mutant of GGBP was overproduced in *E. coli* NM303 ($F^+$ mg1503 lacZlacY$^+$ recA 1) , a mutant strain that does not produce GGBP. The cultures consisted of 0.5% inoculum, 25 $\mu$g/ml ampicillin in 200 mL Luria-Bertani (LB) medium (10 g/L bacto-tryptone, 5 g/L bacto-yeast extract, 10 g/L NaCl, pH 7.2), 1 mM fucose incubated in a 1 L shake flask at 37° C. and 260 rpm. Cells were harvested at 16 h, and GGBP was extracted by osmotic shock as previously described [29]. The crude extract was resuspended in concentrated Tris-HCl and EDTA buffers so that the final concentration was 5 mM and 1 mM, pH 8.0, respectively. The GGBP cysteine mutants also received a final concentration of 1 mM tris(2-carboxyethyl)phosphine (TCEP). The GGBP was purified based on a previous method [30] using a DEAE anion exchange column (Bio-Rad, Hercules, Calif.) and eluting the GGBP with a 5 mM Tris-HCl, pH 8.0 gradient from 0 to 0.5 M NaCl.

Single-cysteine mutant GGBP may be labeled with a single fluorophore as in Example 2 and used as a glucose sensor in which the conformational twist of the protein induced by the binding of glucose causes a change in the environment around the fluorophore. Alternatively, the single-cysteine mutant GGBP labeled with a short lifetime fluorophore may be used in conjunction with a long lifetime fluorophore for lifetime-based modulation sensing as in Example 5.

EXAMPLE 2

Fluorescently Labeled Q26C GGBP

One embodiment of the invention comprises labeling a single cysteine mutant GGBP with 2-(4'-(iodoacetamido) anilino)naphthalene-6-sulfonic acid (I-ANS; see FIG. 6). A solution containing 2.5 mg/ml Q26C GGBP in 20 mM phosphate, 1 mM tris(2-carboxyethyl)phosphine (TCEP), pH 7.0 was reacted with 50 $\mu$L of a 20 mM solution of the sodium salt of I-ANS in tetrahydrofuran (purchased from Molecular Probes, Inc.). The resulting labeled protein was separated from the free dye by passing the solution through a Sephadex G-25 column. The protein-ANS conjugate was purified further on Sephadex G-100.

Figure 7:
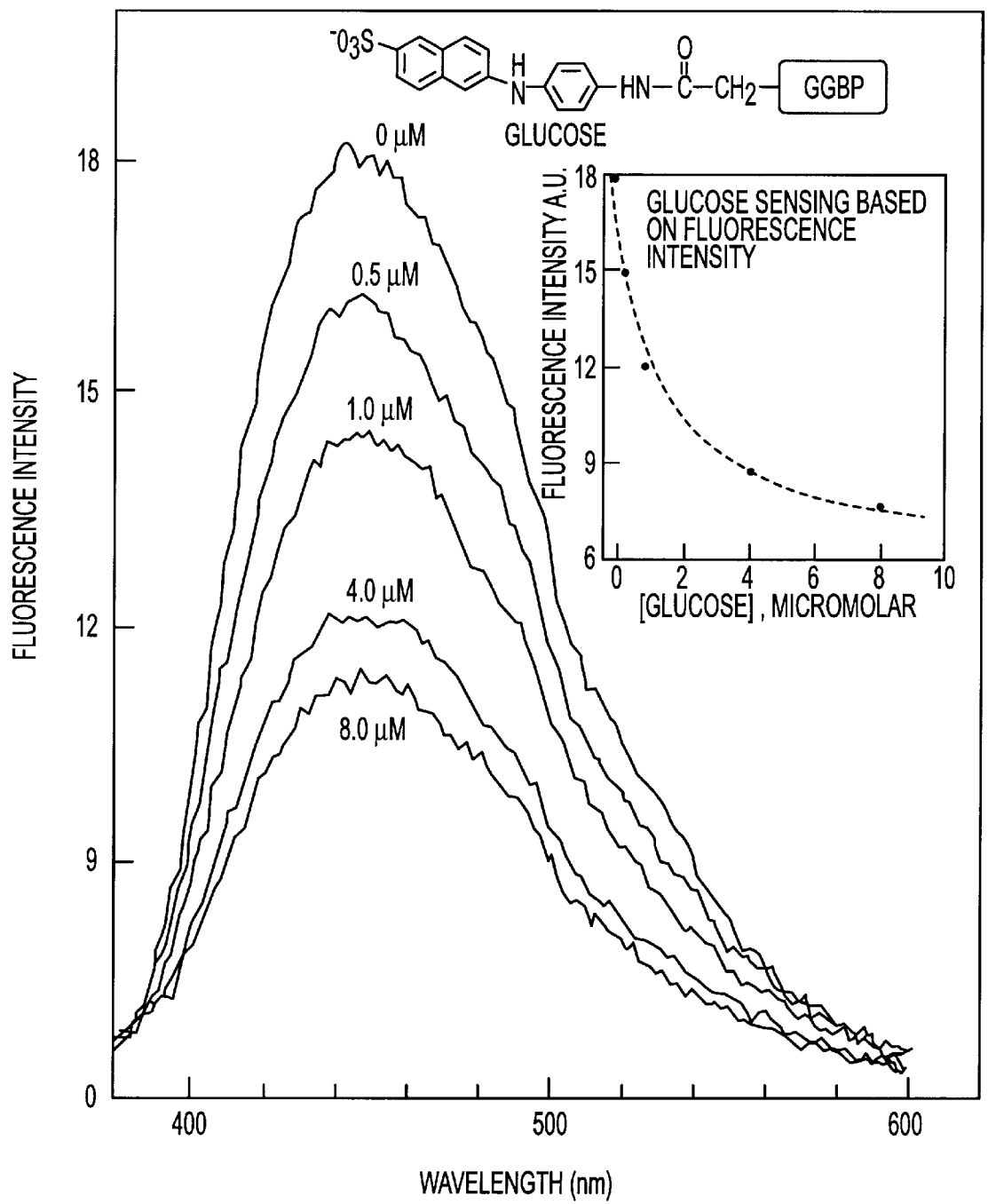
FIG. 7 shows the emission spectra of ANS-Q26 GGBP in the presence of 0 to 8 $\mu$M glucose. GGBP concentration was 0.25 $\mu$M, and excitation was at 325 nm. The insert shows the change in intensity versus glucose concentration.

The emission spectra of ANS26-GGBP are shown in FIG. 7. Addition of micromolar concentrations of glucose resulted in an approximately 2-fold decrease in the intensity of the ANS label, with an apparent dissociation constant near 1 $\mu$M glucose. ANS is known to be sensitive to its local environment with lower intensities in more polar environments [31]. The decrease in intensity suggests that ANS is displaced into the aqueous phase upon binding of glucose to ANS26-GGBP. This is consistent with the glucose-bound structure of GGBP (FIG. 2) where the residue on position 26 is pointing towards the aqueous phase.

EXAMPLE 3

Construction and Labeling of Double-Cysteine Mutant GGBP Glucose Sensors

In this embodiment, the glucose sensor protein operates by interactions between fluorophores on separate domains of a protein which changes in response to glucose binding. In order to obtain fluorescent labels on each domain of the GGBP, a double cysteine mutant was prepared by means similar to that described in Example 1 (see FIG. 5), in which cysteine residues were genetically inserted at positions 26 and 182. The double-cysteine mutant was cultured in GC medium (30 g/L casamino acids, 20 g/L yeast extract) containing 40 g/L glycerol, 4 mM $MgSO_4$, 25 $\mu$g/ml ampicillin and 1 mM fucose. Cells were cultured at the same conditions as for the mono-cysteine mutant, and osmotic shock was used to extract the GGBP. The final buffer was 20 mM Tris, pH 7, 1 mM DTT and EDTA. Contaminating proteins were precipitated with ammonium sulfate. The supernatant was concentrated and the buffer changed to 2 M ammonium sulfate. The GGBP was purified with the Biocad Sprint perfusion chromatography system (PE Corp.) on a hydrophobic interaction media (POROS 20 PE, PE corp.) with a 2 to 0 M ammonium sulfate gradient. The labeled GGBP was separated using the same method with a 1.5 to 0 M gradient.

Figure 8:
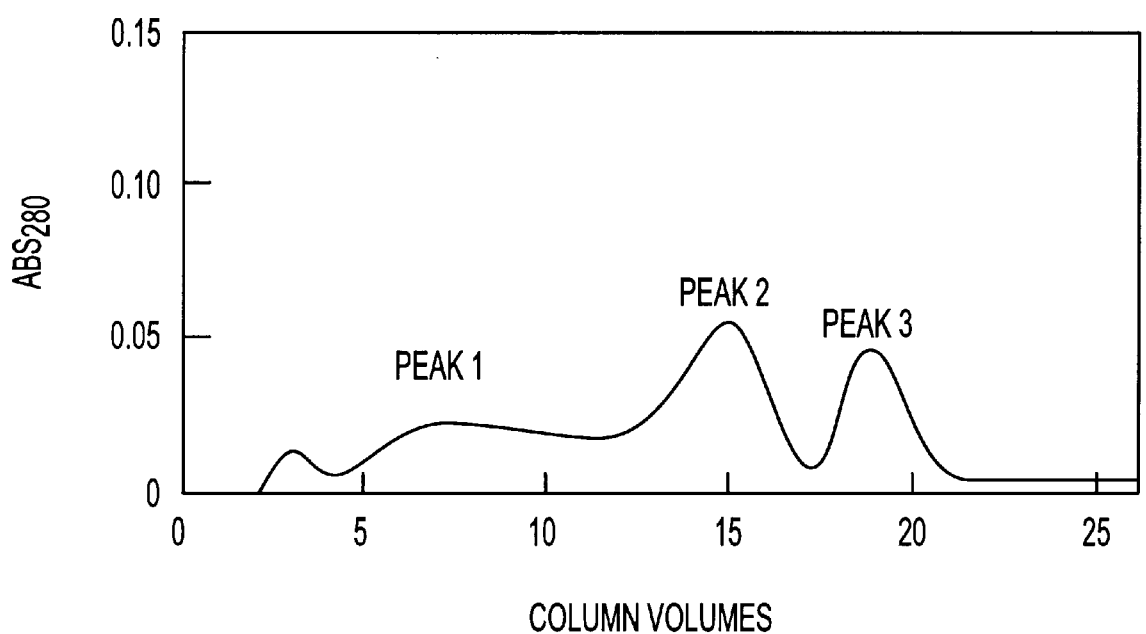
FIG. 8 shows the elution of the Q26C/M182C dicysteine mutant of GGBP after reaction with pyrene maleimide and TEMPO iodoacetamide. Separation was accomplished by hydrophobic interaction chromatography. Fractions containing the pyrene chromophore are designated as peaks 1, 2 and 3.

The double mutant was then reacted with pyrene maleimide, a fluorophore, and TEMPO-iodo-acetamide, a quencher or resonance energy transfer ("RET") acceptor for pyrene. TEMPO was chosen because of the possibility of either collisional quenching by the nitroxide group or RET to the longer wavelength absorption bands of TEMPO. The protein was reacted in such a way that we expected to obtain one pyrene residue and one TEMPO residue on each cysteine residue. The reacted protein was chromatographed and 3 peaks which apparently contained the pyrene chromophore were observed, as shown in FIG. 8.

Figure 9:
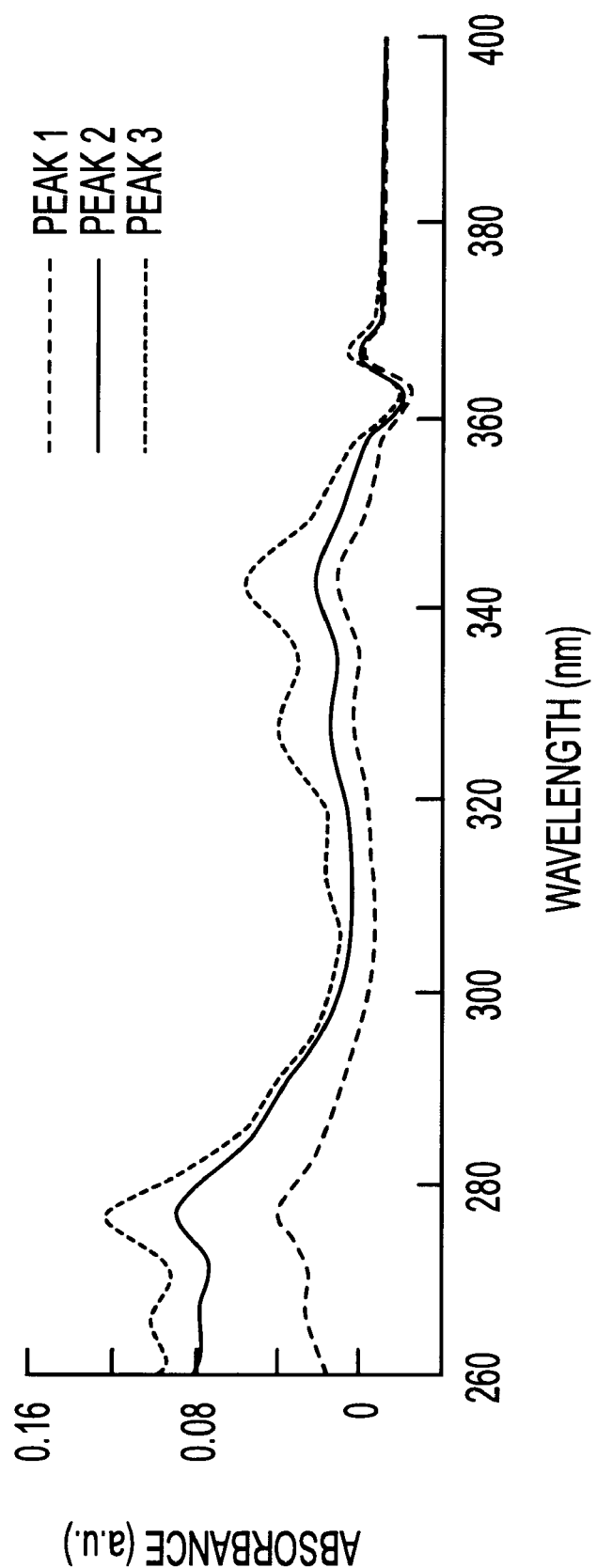
FIG. 9 shows the absorption spectra of peaks 1, 2 and 3 from FIG. 8. Total protein in each solution is 1 $\mu$M.

The samples were chromatographed and the column fractions were pooled based on the ratio absorption at different wavelengths. Absorption spectra of the three main peaks are shown in FIG. 9. These absorption spectra show that each of the peaks contained the pyrene chromophore, as seen from the structured absorption from 300 to 350 nm.

Figure 10:
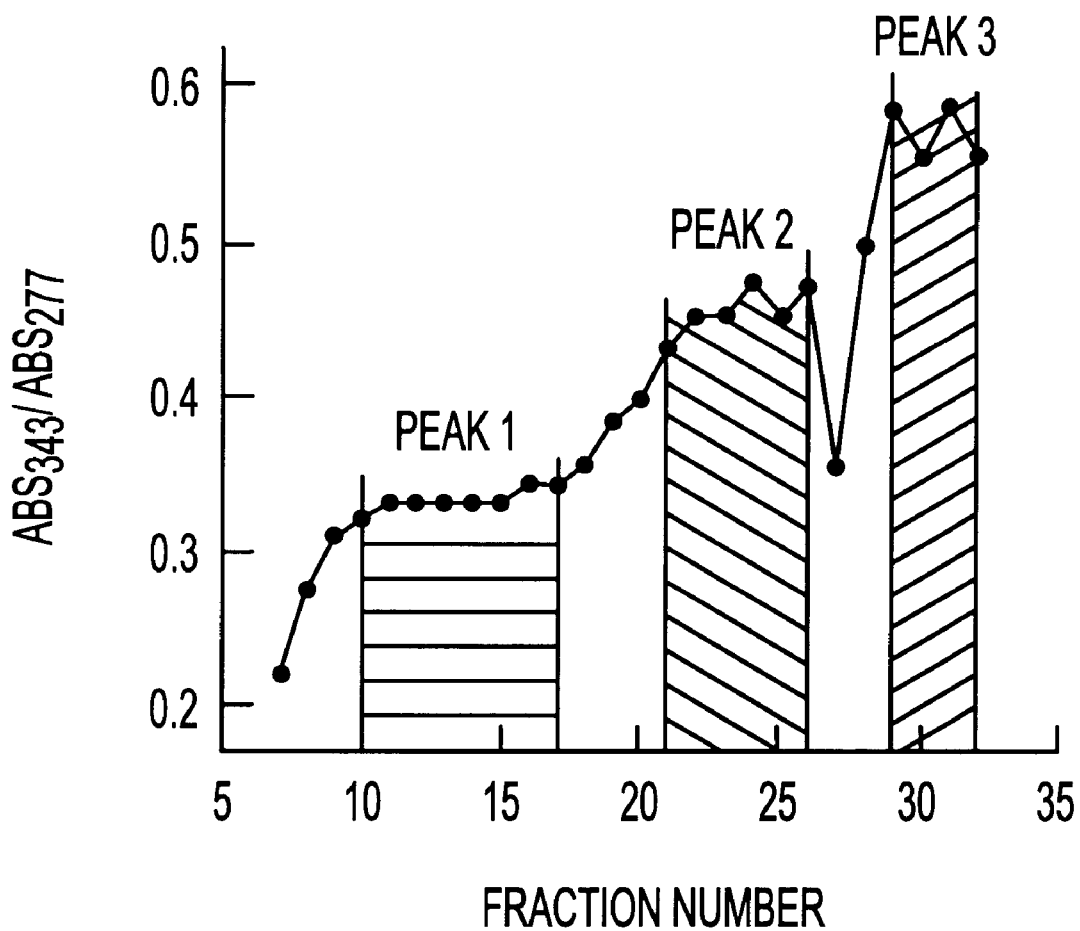
FIG. 10 shows the ratios of absorbancies at 343 and 277 nm across the chromatographic elution profile for the fractions from FIGS. 8 and 9. Shaded areas indicate fractions that were pooled.

FIG. 10 shows the ratio of absorbancies at 343 to 277 nm for the different fractions from the chromatograph. Peak 3 contains the largest amount of pyrene per protein molecule. Calculations based on the extinction coefficient of pyrene at 343 nm and the total amount of protein assayed using Coomasie Blue showed that peak 3 contains two pyrene molecules per protein.

Figure 11:
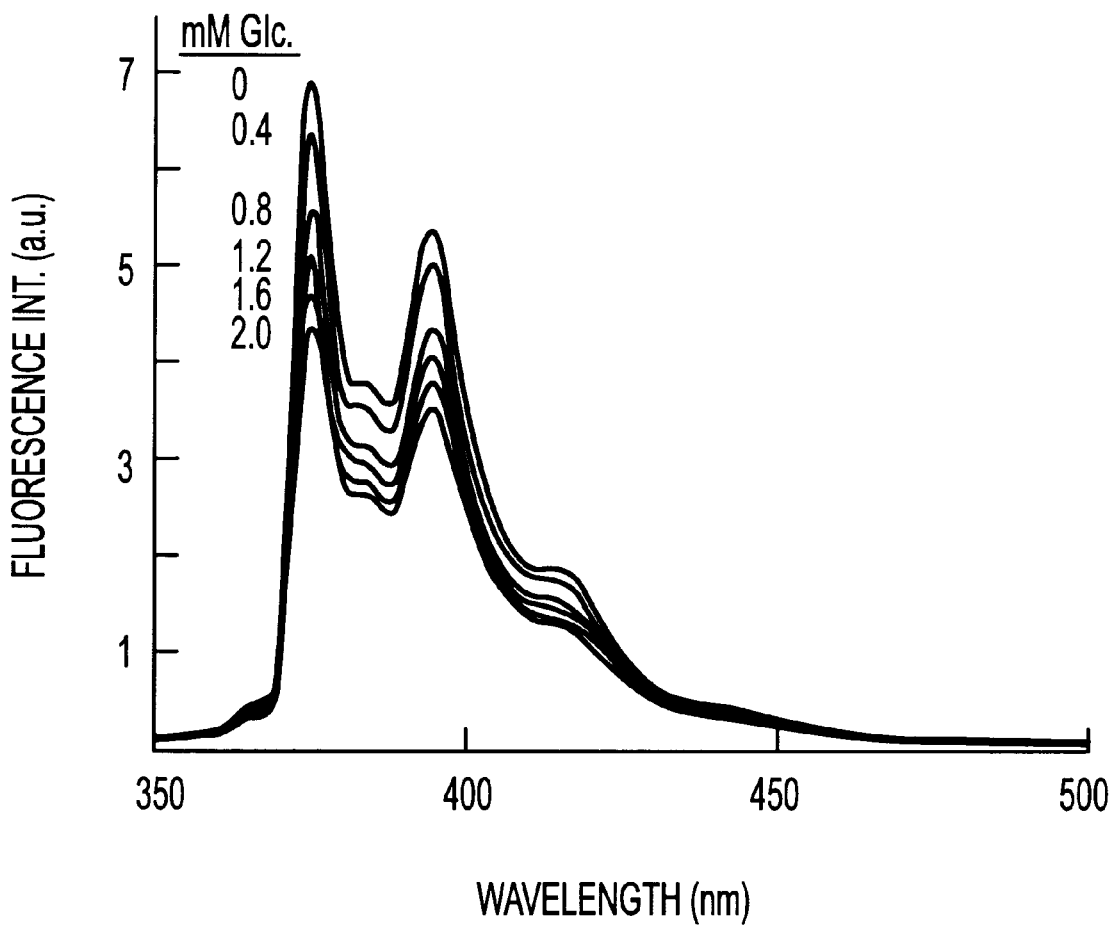
FIG. 11 shows the emission spectra of labeled GGBP-peak 2 (from FIG. 8) as a function of glucose concentration.

Similar calculations for peak 2 showed one pyrene per protein molecule. The single cysteine mutant, Q26C, labeled with pyrene maleimide exhibited identical properties, thereby indicating that peak 2 is most likely labeled with pyrene at the 26-position and TEMPO at the 182-site. The emission spectra from peak 2 (FIG. 11) is very characteristic of pyrene. The emission drops close to zero at 450 nm, which indicates the absence of excited state complex formation (excimer of pyrene) with itself or other molecules which form excimers or exciplexes with pyrene.

Peak 1 appears to contain the least amount of pyrene per protein molecule (FIG. 10), but it is likely that the absorbance spectrum is simply broadened by ground state interactions with nearby residues. That may also explain the unusual shape of the emission spectrum (not shown).

Figure 12:
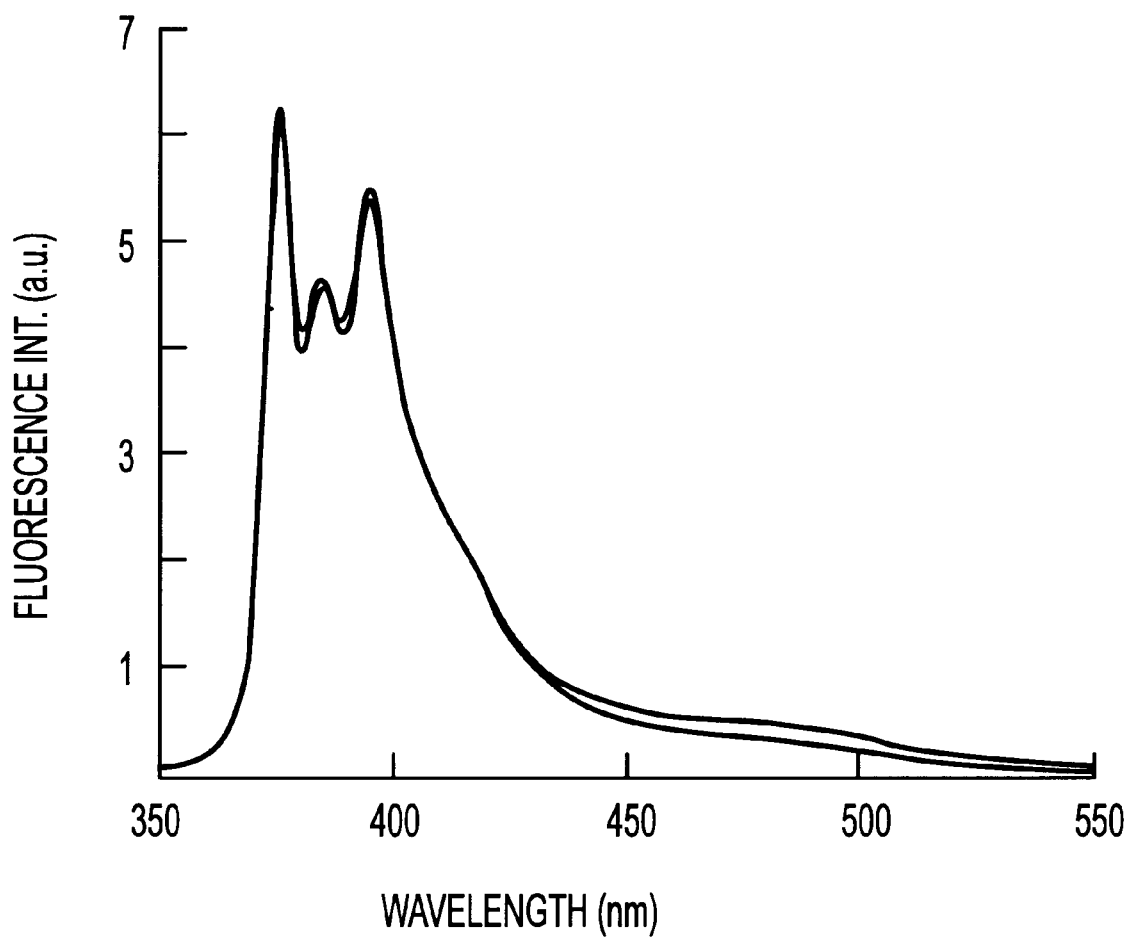
FIG. 12 shows the emission spectra of labeled GGBP-peak 3 (from FIG. 8) with and without 2 mM glucose.

FIG. 12 shows the emission spectra of peak 3 which is believed to be labeled with two pyrene residues per protein. The evidence for this assertion is the presence of a longer wavelength emission from 450–500 nm. Such an emission is typical of two interacting pyrene residues which are known to form excited state complexes which display longer wavelength emission. Free pyrene in solution is also known to form excimers, but this would not occur at the 0.5 micromolar protein concentration in peak 3.

Figure 13:
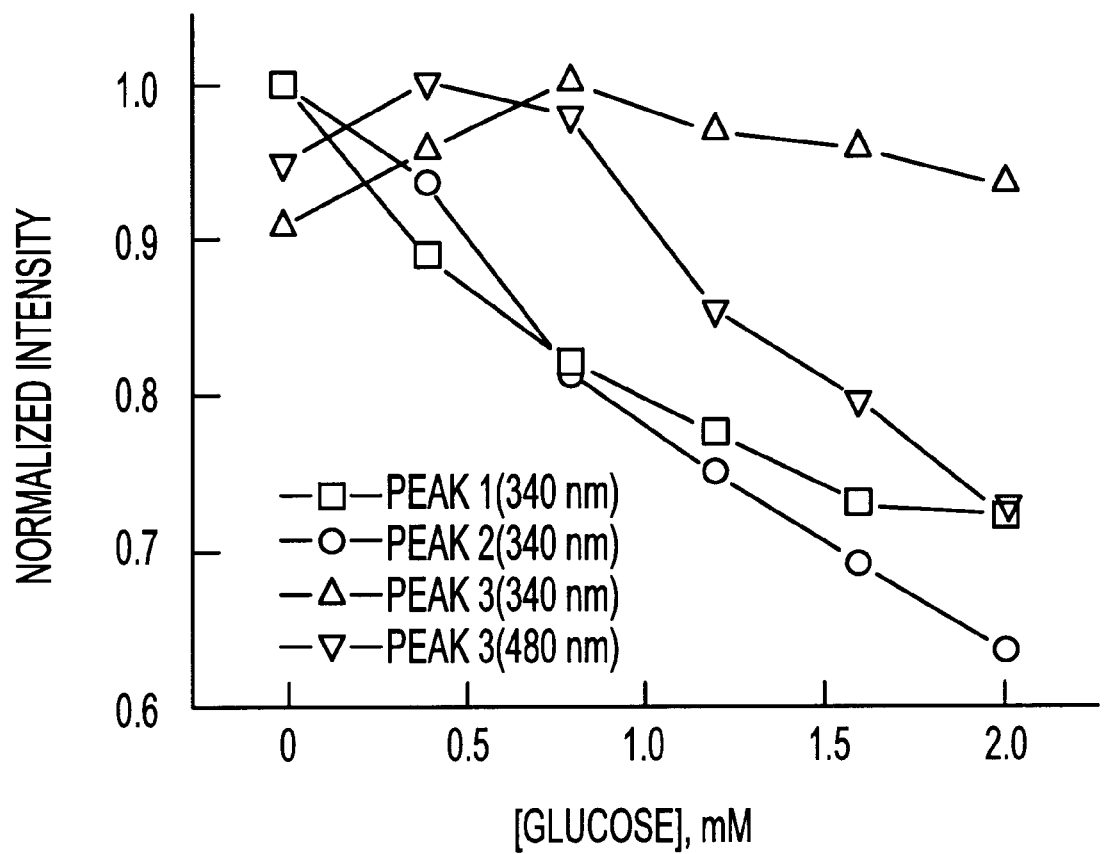
FIG. 13 shows the normalized fluorescence intensities measured at 384 nm for peaks 1, 2 and 3 (from FIG. 8) as a function of glucose concentration. The excitation wavelength was 340 nm. In the case of peak 3, the emission was also measured at 480 nm.
Figure 14:
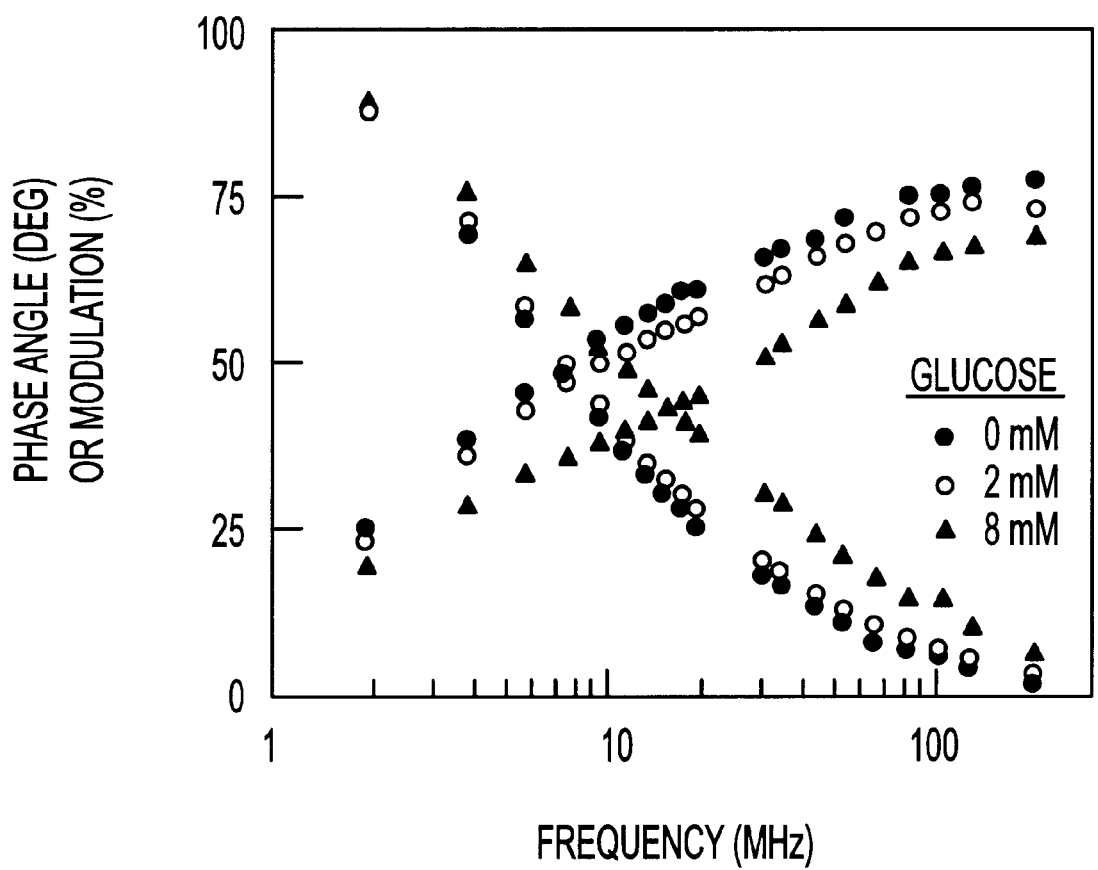
FIG. 14 shows the frequency-domain lifetime measurements of GGBP-peak 3 (from FIG. 8) at various glucose concentrations. The shift to lower frequencies at higher glucose concentrations indicates that the mean lifetime decreased on glucose binding.
Figure 15:
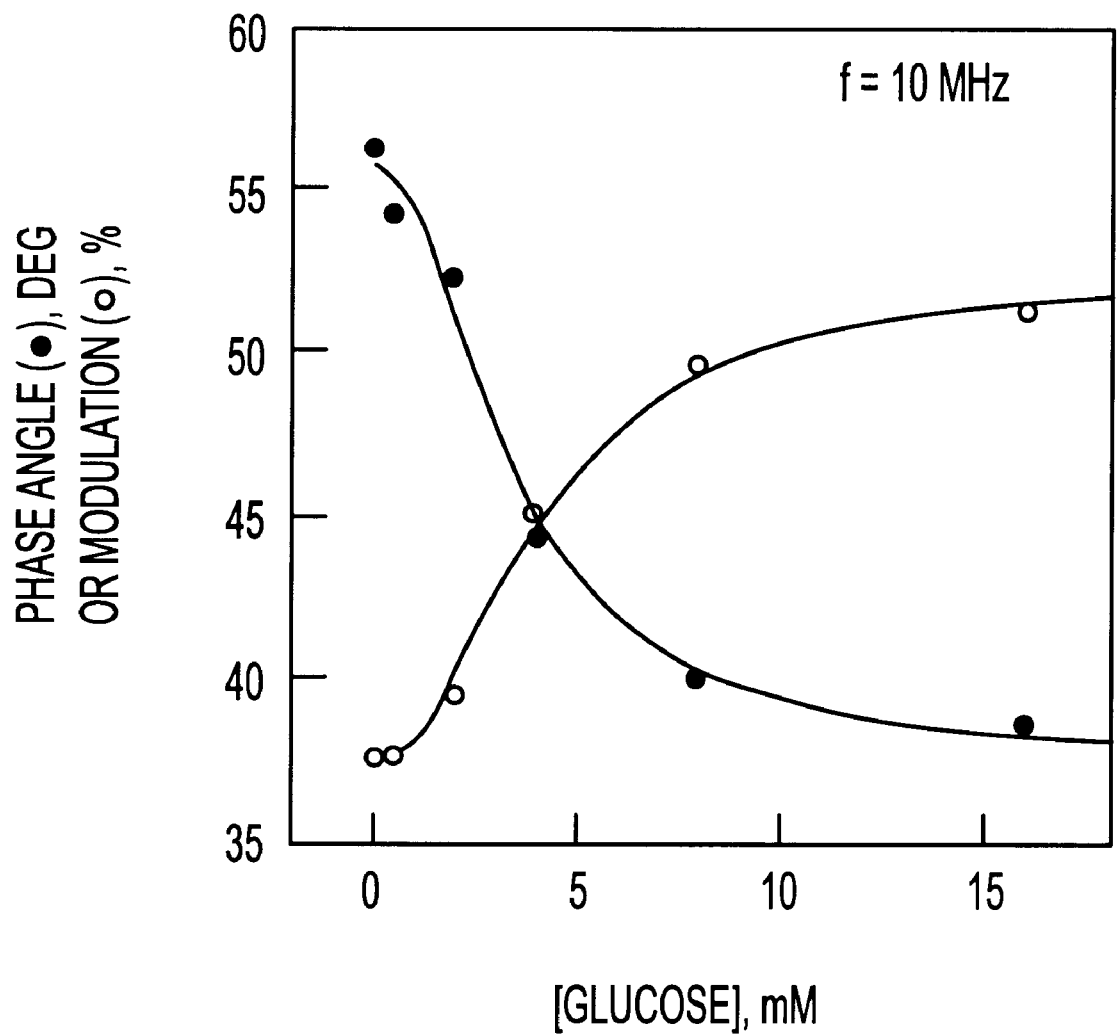
FIG. 15 shows the lifetime-based sensing of glucose based on the phase or modulation data at 10 MHZ.

FIG. 13 shows the normalized intensities of the three fractions with added glucose. In the case of fraction 3, we looked at the intensities both at the monomer emission of 384 and the excimer emission at 480 nm. The most promising results were obtained for the excimer emission which decreased by 30% upon addition of glucose. The frequency-domain intensity decay of the 480 nm emission from peak 3 is shown in FIG. 14. The frequency response was strongly dependent on glucose indicating a change in the mean lifetime of the labeled protein upon glucose binding. FIG. 15 shows the phase and modulation data at 10 MHz, which also demonstrates a lifetime changed upon glucose binding. These data demonstrate that mutant GGBP can be used with lifetime-based sensing for glucose measurements.

EXAMPLE 4

Labeled Mutant GGBP Glucose Sensor for Energy Transfer

There can be difficulties with selectively labeling a protein with two cysteine residues as is needed for a glucose sensor that operates by energy transfer. Therefore, this invention includes embodiments wherein fusion proteins of GGBP or its mutants are created.

Figure 16:
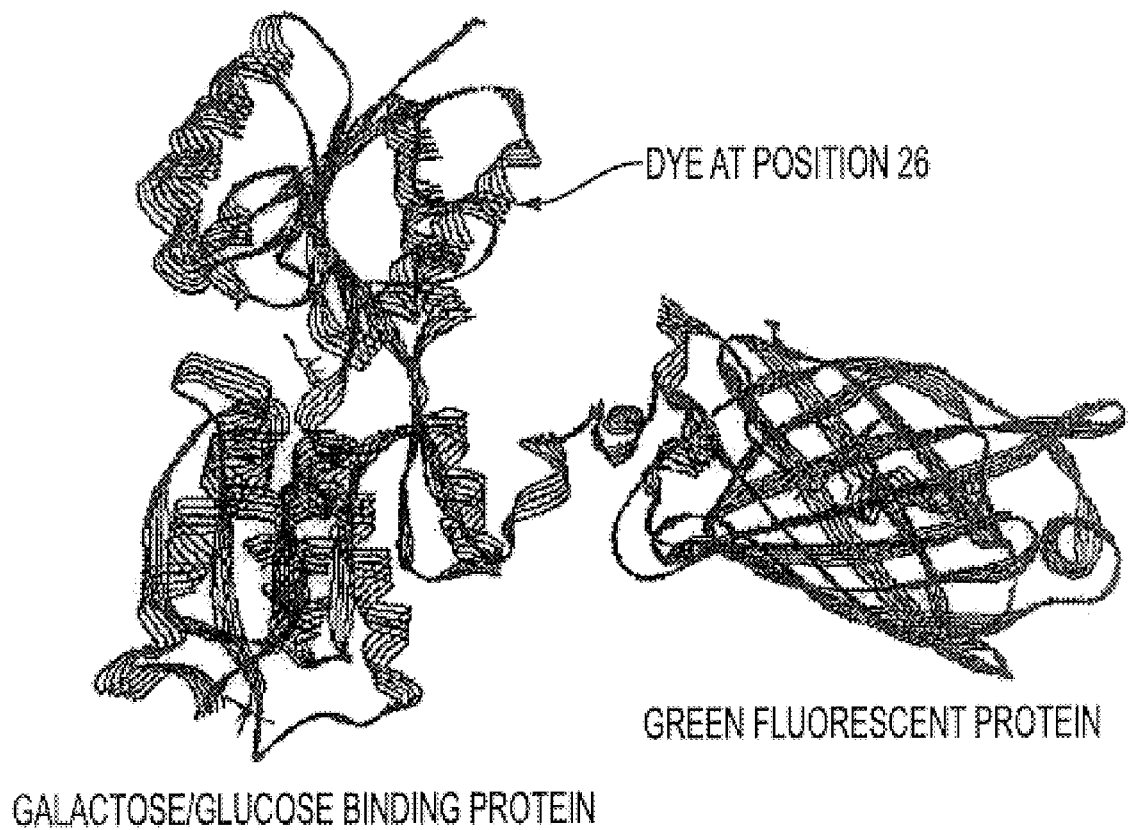
FIG. 16 depicts the tertiary crystal structure of a mutant GGBP fusion protein with green fluorescent protein(GFP) at the C-terminus and a reactive cysteine and thiol-reactive dye at position 26 (Q26C-GGBP-GFP).
Figure 17:
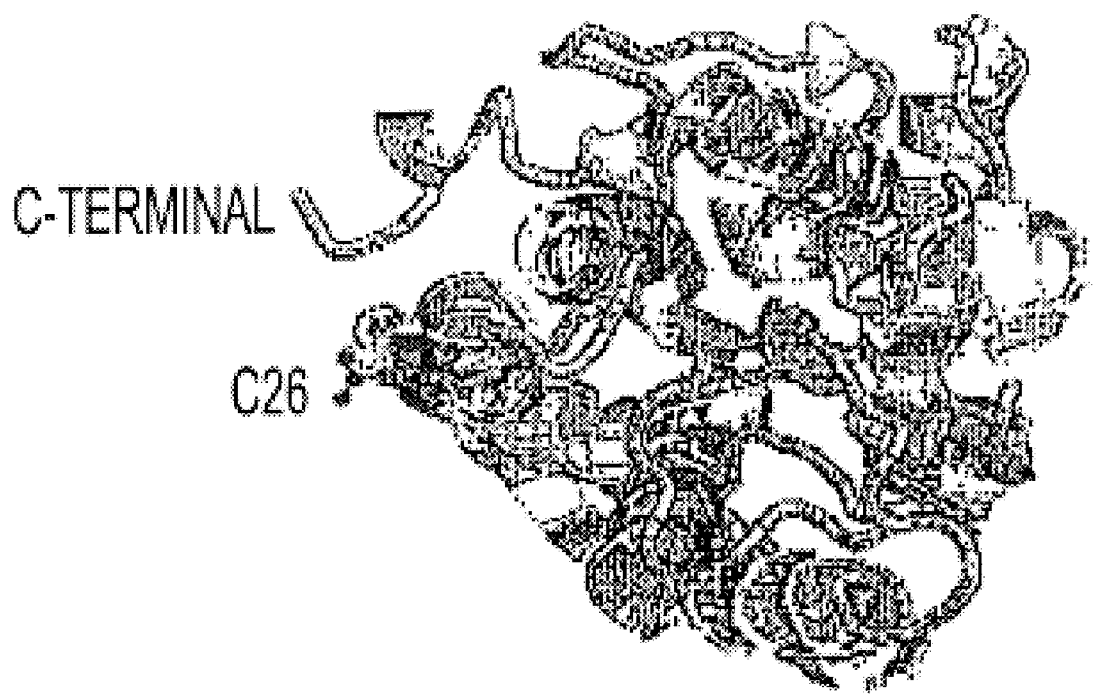
FIG. 17 depicts that the relative positions of C26 and the C-terminal of a Q26C-GGBP are closer upon glucose binding (crystal structure from protein data).

In one embodiment, the mono-cysteine mutant GGBP with a reactive cysteine and dye at position 26 is a fusion protein with a fluorophore at the C-terminus. This is shown schematically in FIG. 16. In this case, the protein needs to be only labeled with one fluorophore at a unique cysteine residue. This should be simpler and more efficient than labeling the dicysteine mutant. The distance between the cysteine residue and the C-terminus should change upon glucose binding (FIG. 17) resulting in a change in lifetime, energy transfer, intensity or anisotropy.

In this embodiment, for example, the two fluorophores may include a donor molecule Green Fluorescent Protein at the C-terminal and an acceptor molecule dye at position 26. The donor and acceptor molecules are so positioned on GGBP such that binding of glucose causes a conformational change to the GGBP pushing apart the donor and acceptor fluorophores so that emission from the donor fluorophore is no longer quenched by absorbance by the acceptor fluorophore. The glucose binding thereby causes an increase in fluorescence of the labeled mutant GGBP (see FIG. 3)

Figure 18:
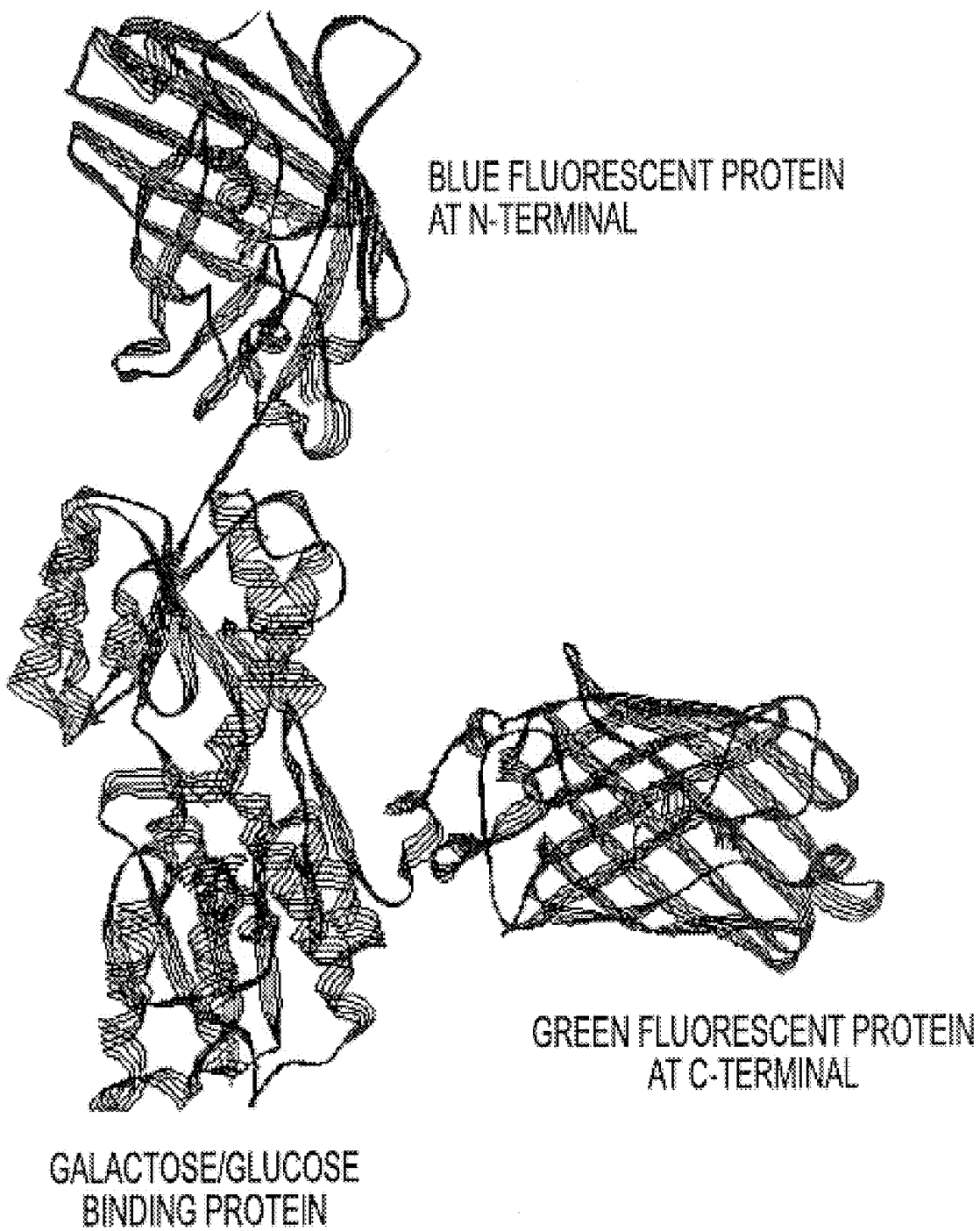
FIG. 18 depicts the tertiary crystal structure of a GGBP fusion protein with blue fluorescent protein (BFP) at the N-terminal and GFP at the C-terminal (BFP-GGBP-GFP) in the presence of bound glucose.
Figure 19C:
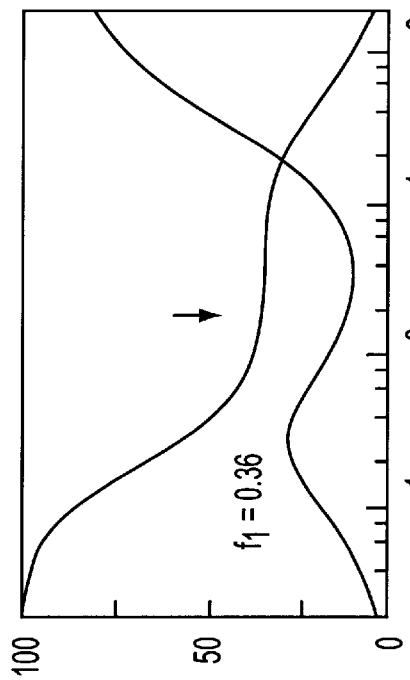
FIG. 19 shows the simulated frequency-domain intensity decays for a mixture of fluorophores, $\tau_1$=5 ns, $\tau_2$=1000 ns, $f_1$=0.76 to 0.1.
Figure 19D:
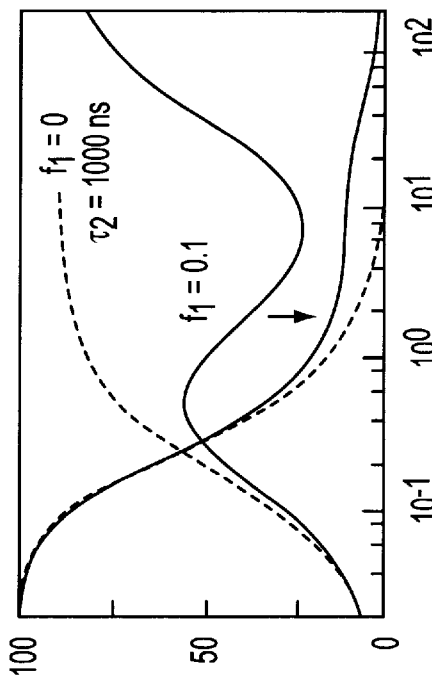
Figure 19A:
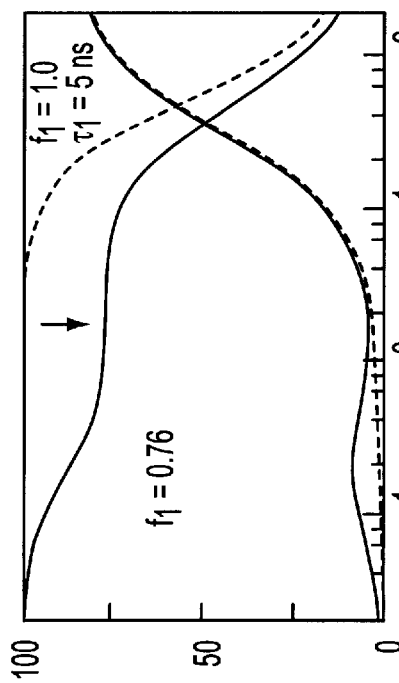
Figure 19B:
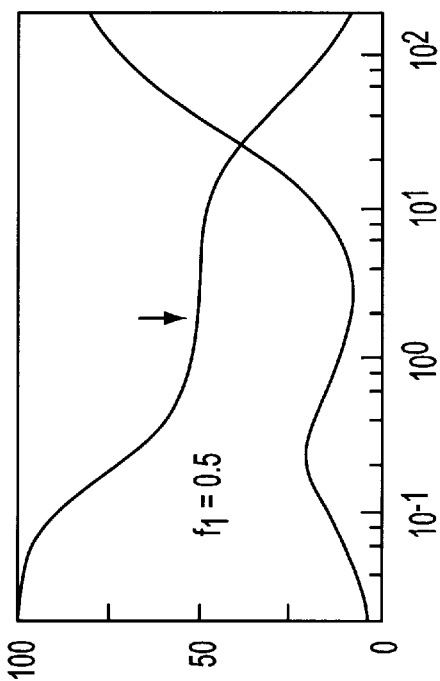

Yet another embodiment may include a GGBP fusion protein with fluorophores at both the C-terminal and N-terminal positions. One non-exclusive example is illustrated in FIG. 18, wherein a donor molecule Green Fluorescent Protein is attached at the C terminal and an acceptor molecule Blue Fluorescent Protein is attached at the N-terminal of GGBP. In this case there would be no need to further label the protein following its synthesis by *E. Coli*. The conformational change occurring upon binding of glucose would cause a change in efficiency of energy transfer between the two fluorophores.

In this embodiment, the donor and acceptor molecules are so positioned on GGBP such that binding of glucose causes a conformational change to the GGBP. This conformational change brings the donor and acceptor fluorophores closer together so that emission from the donor fluorophore GFP is quenched by absorbance by the acceptor fluorophore BFP. The glucose binding thereby causes a decrease in fluorescence of the labeled mutant GGBP (see FIG. 4).

EXAMPLE 5

Simulation of Low-frequency Modulation-based Glucose Sensor

The glucose-sensitive intensity of ANS26-GGBP makes this protein a potential component in the design of another embodiment of the invention: a low-frequency modulation-based glucose sensor. A description of the theory behind modulation sensors is provided in a paper by Lakowicz, et al., [32]. This embodiment uses lifetime-based sensing techniques, in which fluorophores or sensing schemes are identified that display an analyte-dependent change in the sample's decay time, and the change in decay time is used to determine the concentration of the analyte. The basic idea is to use a mixture of the nanosecond fluorophore with a fluorophore that displays a long lifetime near 1 $\mu$s. For such a mixture the modulation of the emission at intermediate frequencies becomes equivalent to the fraction of the total emission due to the short lifetime nanosecond fluorophore. This occurs because the emission from the microsecond fluorophore is demodulated and that of the nanosecond fluorophore is near unity. This method allows sensing based on modulation from about 1 to 10 MHz. Additionally, the nanosecond sensing fluorophore does not need to display a change in lifetime ($\tau$). A simple change in intensity in response to the analyte is adequate for a low-frequency modulation sensor.

Lifetime-based sensing is most often performed using the phase-modulation method. The use of phase angles ($\phi$) or decay times can be preferable to intensity-based sensing because decay times are mostly independent of changes in probe concentration or total signal level and can be measured in turbid media and even through skin [32]. Because the modulation is independent of total signal level, modulation sensing can be accurate even if there are changes in signal level due to changes in the position of the sample or flexing of fiber optics. What is necessary is that the relative proportions of short and long-lifetime fluorophores remain the same. The calibration curve will change if the relative intensities of the fluorophores change in a manner independent of analyte concentration. For example, if the sensing and reference fluorophores photobleach at different rates, the modulation sensor calibration curves will change.

In one embodiment of a modulation sensor, a short-lived glucose-sensitive probe may be combined with a long-lived probe such as a metal-ligand complex. At low frequencies, the modulation of the combined emission of analyte sensitive short-lived probe and the long-lived metal-ligand complex depends on the fractional fluorescence intensity of the shorter lifetime species. The fractional intensity decreases on binding glucose, resulting in a decrease in the modulation which can be used to measure the glucose concentration.

In one preferred embodiment, the glucose sensitive ANS26-GGBP is combined with a long lifetime metal-ligand complex such as [Ru(bpy)$_3$]$^{2+}$. For construction of the sensor, [Ru(bpy)$_3$]$^{2+}$ was dissolved in heated polyvinyl alcohol, which was then painted on the outside of a cuvette which contained the glucose-sensitive protein (ANS26-GGBP). Q26C GGBP was labeled with I-ANS to make ANS26-GGBP as described in Example 2.

Frequency-domain intensity decay were measured with instrumentation described previously [33], modified with a data acquisition card from ISS, Inc., Urbana, Ill. [34]. Excitation was at 325 nm from a HeCd laser modulated with a Pockels cell. Emission spectra were recorded on an Aminco SLM AB2 spectrofluorometer using an excitation wavelength of 325 nm. Polarizers were used to eliminate the effect of Brownian rotation. The concentration of ANS26-GGBP was 0.25 $\mu$M. The fluorescence spectra are relative to an identical reference sample that was sugar-free.

Figure 20:
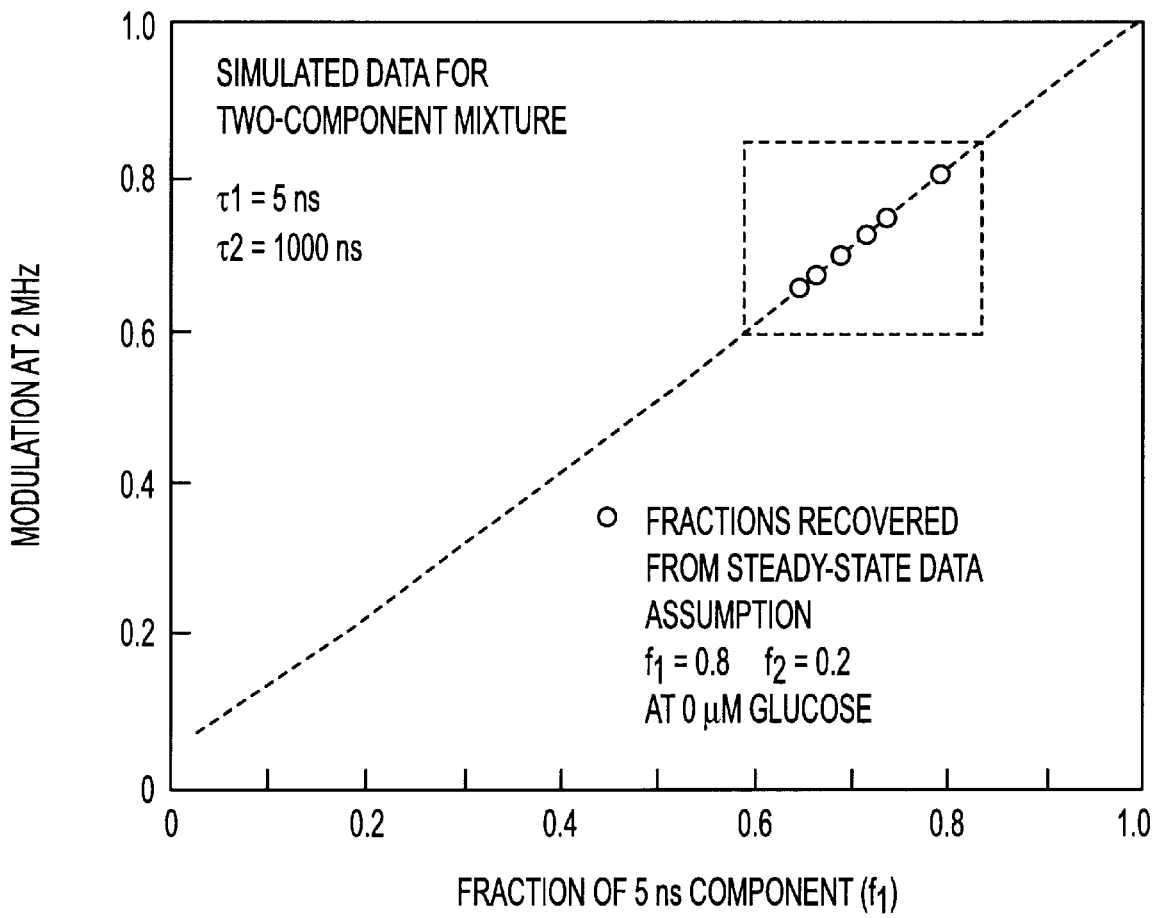
FIG. 20 shows the simulated dependence of the modulation at 2 MHZ on the fractional intensity ($f_1$) of the 5 ns component.

Simulated frequency-domain data for a mixture of fluorophores are shown in FIG. 19. The lifetimes were assumed to be $\tau_1=5$ ns and $\tau_2 1000$ ns=1 $\mu$s. The lifetime of 5 ns is comparable to the mean lifetime of ANS-GGBP. Metal-ligand Re complexes with lifetimes of over 1 $\mu$s are now available, so that 1 $\mu$s fluorophores are available. For these simulations we assumed the fractional intensity of the 5 ns changed from 0.1 to 0.76. There is a region near 2 MHz where the modulation is almost independent of modulation frequency. Importantly, the modulation is sensitive to the fractional intensity of the short lived component. For the assumed lifetimes the modulation at 2 MHz is nearly equal to the amplitude of the short lived component. This is shown in FIG. 20, which indicates that the modulation at 2 MHz is essentially equivalent to the fractional amplitude of the short lifetime component. This result can be easily understood by noting that the modulation of the 5 ns component is near 1.0 at 2 MHz, and the modulation of the 1 $\mu$s component is near zero at 2 MHz.

Figure 21:
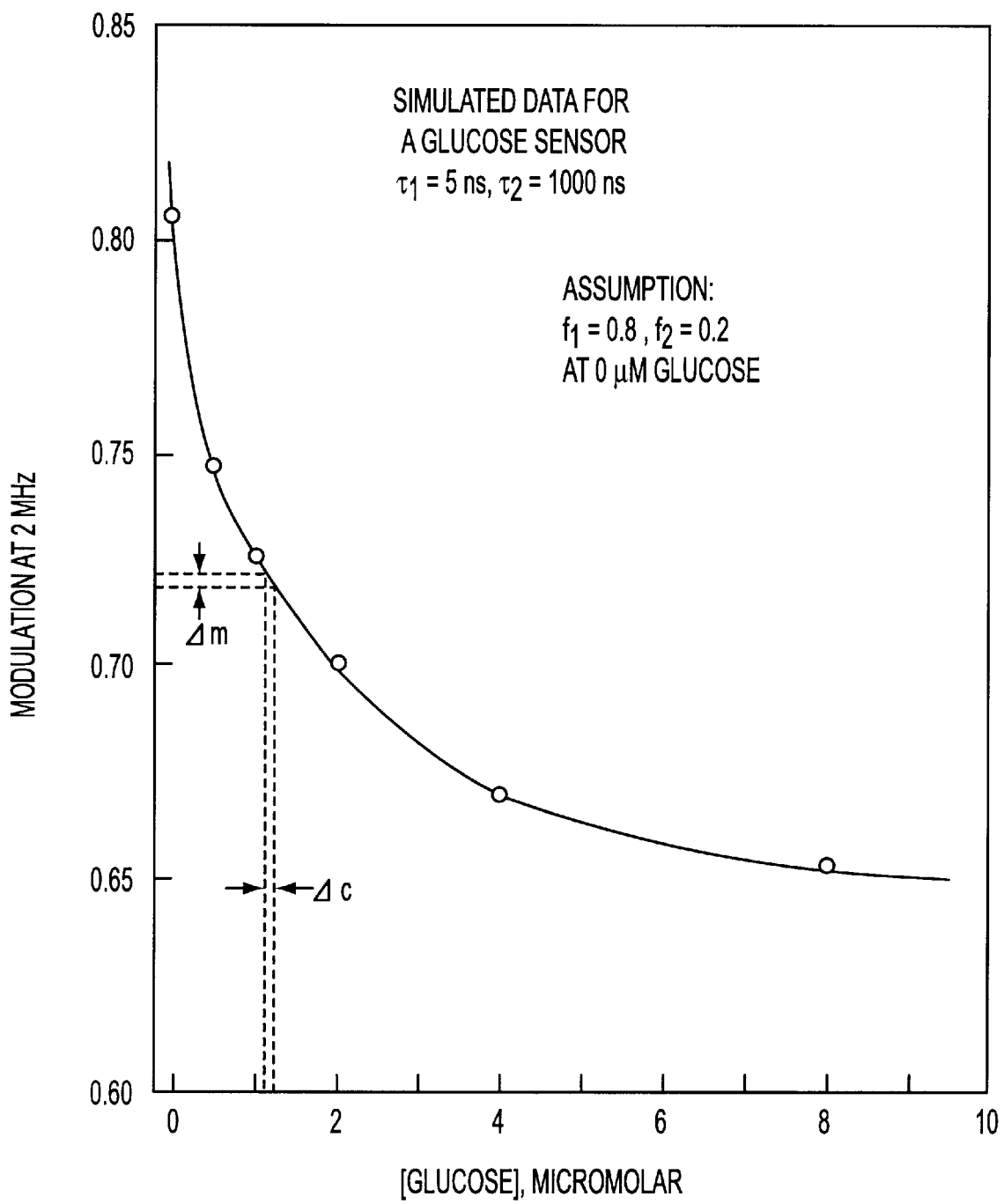
FIG. 21 shows the simulated modulation for a glucose sensor with $\tau_1$=5 ns, $\tau_2$=1000 ns.

The accuracy in glucose concentration expected for such a modulation sensor based on a mixture with lifetime of $\tau_1=5$ ns and $\tau_2=1$ $\mu$s was calculated from changes in modulation which could be expected for the 2-fold intensity changes displayed by GGBP (FIG. 21). For this glucose-sensitive protein the two-fold decrease in intensity of GGBP could decrease the modulation of 2 MHz from 0.81 to 0.66 (FIG. 21). The modulation can be measured routinely to an accuracy of 0.005, which would result in glucose concentrations around to +0.2 $\mu$M. We note that a larger change in intensity of the glucose-sensitive emission would result in larger changes in modulation and higher accuracy in the glucose concentration. Also, with dedicated instruments the modulation may be measured to higher accuracy.

Figure 22:
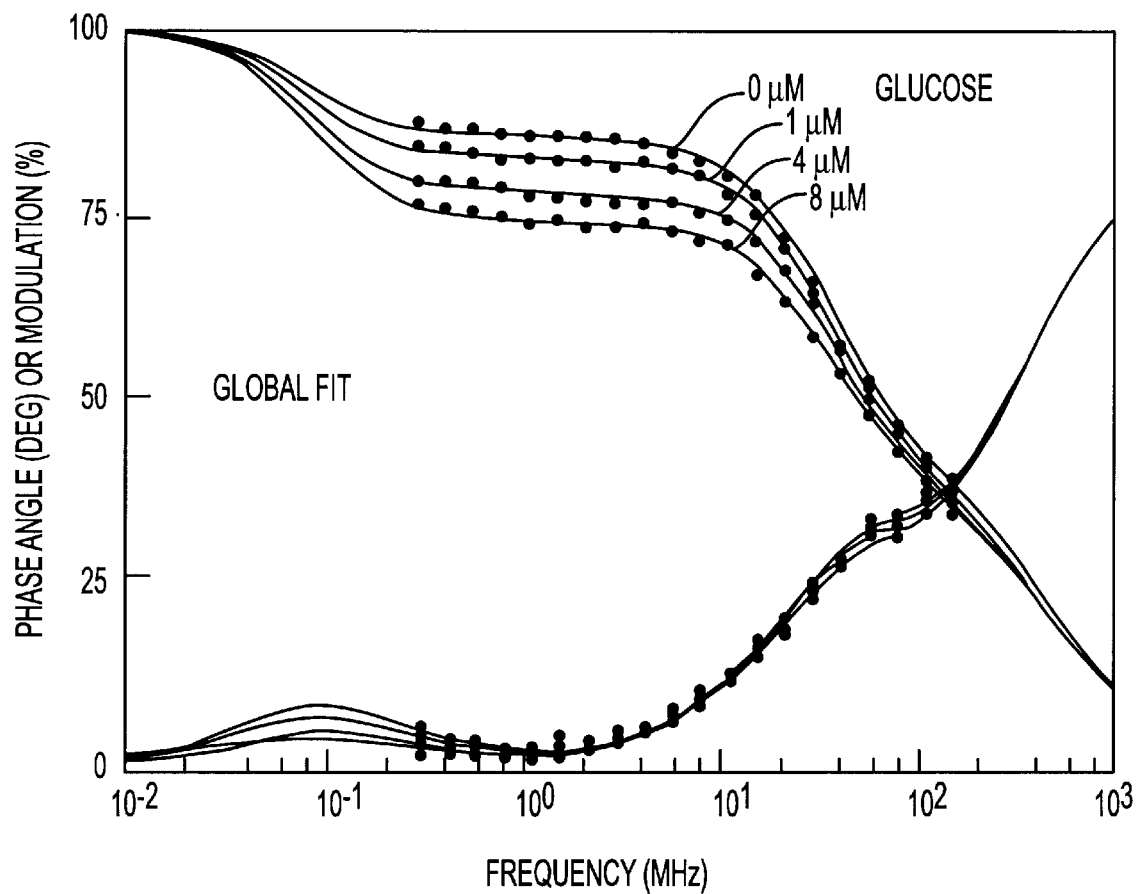
FIG. 22 shows the frequency responses of the glucose sensor at 0, 1, 4 and 8 $\mu$M glucose.
Figure 23:
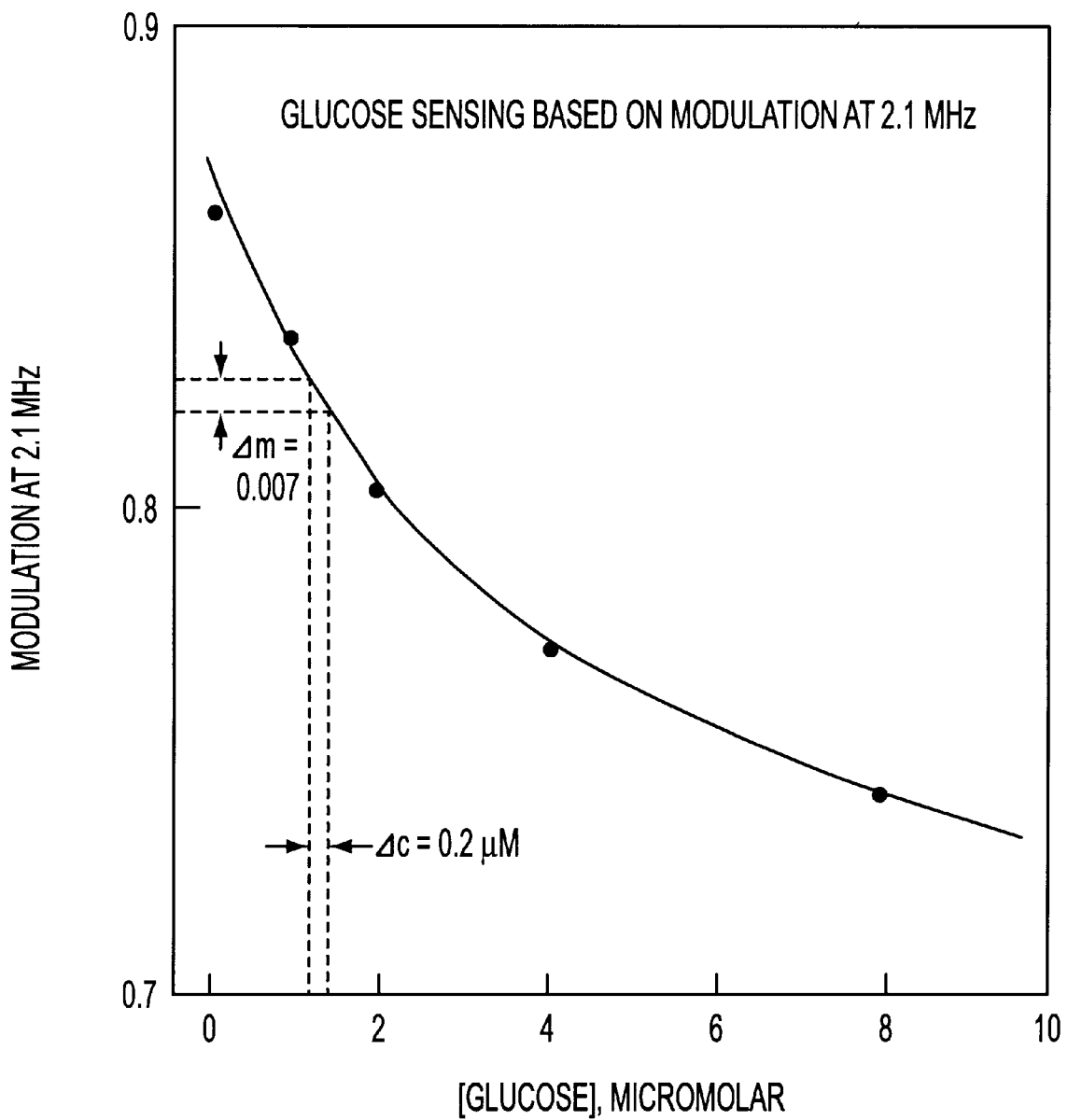
FIG. 23 shows the effect of glucose on modulation of the glucose sensor at 2.1 MHZ.

To measure glucose, the labeled protein ANS26-GGBP was placed adjacent to the ruthenium complex to result in a fractional GGBP intensity near 0.87 in the absence of glucose. The Ru complex was in a thin PVA film outside the cuvette containing ANS26-GGBP. Frequency responses are shown in FIG. 22. These responses are comparable to the simulations shown in FIG. 19. Importantly, the modulation at 2.1 MHz decreases in the presence of glucose, as expected for decreased emission for ANS26-GGBP. These changes in modulation were used to prepare a calibration curve for glucose (FIG. 23). These data demonstrate that the ANS26-GGBP can be used to quantify micromolar concentrations of glucose. Modulation measurements accurate to $\Delta m=\pm 0.007$ would result in glucose concentrations accurate to $\Delta c=\pm 0.2$ $\mu$M. We expect future labeled GGBP mutants will display large changes in fluorescence and to yield more accurate glucose measurements.

The short and long lifetime components in this simulated embodiment were physically separated to avoid interactions of the long lived ruthenium complex with GGBP. Such a physical separation can be readily accomplished in a sensor that, for example, comprises two polymeric layers, one containing labeled GGBP and the other containing the long-lifetime complex. Alternatively, one may choose other long lived fluorophores which do not interact with the protein, such as the highly charged ruthenium complex proposed recently as a water-soluble oxygen sensor [35]. This invention includes sensors that comprise two polymeric layers and long-lived fluorophores that do not react with GGBP.

Other embodiments of the modulation-based sensor may include long lifetime metal-ligand complexes such as, but not limited to, rhenium and osmium. For the short lifetime sensor component, any sensing fluorophore that changes intensity can be used, and is included in this invention; a change in probe lifetime is not needed.

In considering the opto-electronics required for modulation based sensing, blue light emitting diodes (LEDs) can be amplitude modulated from 0.1 to 100 MHz [36], and LEDs with ultraviolet output near 380 nm are available and can be modulated to 100 MHz [27]. Electroluminescent devices can also be modulated at MHz frequencies [28]. Hence, simple inexpensive light sources could be used for a modulation glucose sensor.

A device for modulation-based sensing can be simpler than the usual phase-modulation instruments. For phase angle measurements the detector must be modulated with a fixed phase relationship to the modulated excitation. Modulation measurements can be performed without the phase-locked relationship, simplifying the electronics. These considerations suggest that a portable battery powered device can be designed to monitor glucose. The sensitivity of this method to low glucose concentrations suggests its use to monitor glucose in interstitial fluid. Because of the high affinity of GGBP for glucose this device also could be used with diluted blood, as the glucose concentration in whole blood is in the mM range. Recent experiments show the feasibility of constructing low-cost instrumentation for phase-modulation measurements up to 100 MHz [37].

REFERENCES

1. Heise, H. M., Marbach, R., Koschinsky, Th., and Gries, F. A. (1994) Noninvasive blood glucose sensors based on the near-infrared spectroscopy, *Artif. Organs* 18(6):439–447.
2. Robinson, M. R., Eaton, R. P., Haaland, D. M., Koepp, G. W., Thomas, E. V., Stallard, B. R., and Robinson, P. L. (1992) Noninvasive glucose monitoring in diabetic patients: a preliminary evaluation, *Clin. Chem.* 38(9):1618–1622.
3. Burmeister, J. J., Chung, H., and Arnold, M. A. (1998) Phantoms for noninvasive blood glucose sensing with near infrared transmission spectroscopy, *Photochem. Photobiol.* 67(1):50–55.
4. March, W. F., Rabinovitch, B., Adams, R., Wise, J. R., and Melton, M. (1982) Ocular glucose sensor, *Trans. Am. Soc. Artif. Intern. Organ.* 28:232–235.
5. Rabinovitch, B., March, W. F., and Adams, R. L. (1982) Noninvasive glucose monitoring of the aqueous humor of the eye: Part I. Measurement of very small optical rotations, *Diabetes Care* 5(3):254–258.
6. Claremont, D. J., Sambrook, I. E., Penton, C., and Pickup, J. C. (1986) Subcutaneous implantation of a ferrocene-mediated glucose sensor in pigs, *Diabetologia* 29:817–821.
7. Yokoyama, K., Sode, K., Tamiya, E., and Karube, I. (1989) Integrated biosensor with glucose and galactose, *Anal. Chim. Acta.* 218:137–142.
8. Schier, G. M., Moses, R. G., Gan, 1. E. T., and Blair, S. C. (1988) An evaluation and comparison of reflolux II and glucometer II, two new portable reflectance meters for capillary blood glucose determination, *Diabetes Res. Clin. Practice* 4:177–181.
9. Clarke, W., Becker, D. J., Cox, D., Santiago, J. V., White, N. H., Betschart, J., Eckenrode, K., Levandoski, L. A., Prusinki, E. A., Simineiro, L. M. Snyder, A. L., Tideman, A. M., and Yaeger, T. (1988) Evaluation of a new system for self blood glucose monitoring, *Diabetes Res. Clin. Practice* 4:209–214.
10. Meadows, D., and Schultz, J. S. (1988) Fiber-optic biosensors based on fluorescence energy transfer, *Talanta* 35(2):145–150.
11. Shultz, J. S., Mansouri, S., and Goldstein, I. J. (1982) Affinity sensor: a new technique for developing implantable sensors for glucose and other metabolites, *Diabetes Care* 5(3):245–253.
12. Schultz, J. S. and Sims, G. (1979) Affinity sensors for individual metabolites, *Biotechnol. Bioeng. Symp.* 9:65–71.
13. Lakowicz, J. R. and Maliwal, B. P. (1993) Optical sensing of glucose using phase-modulation fluorometry, *Anal. Chim. Acta.* 271:155–164.
14. Tolosa, L., Szmacinski, H., Rao, G., and Lakowicz, J. R. (1997) Lifetime-based sensing of glucose using energy transfer with a long lifetime donor, *Anal. Biochem.* 250:102–108.
15. Tolosa, L., Malak, H., Rao, G., and Lakowicz, J. R. (1997) Optical assay for glucose based on the luminescence decay time of the long wavelength dye Cy5™, *Sensors and Actuators B* 45:93–99.
16. Marvin, J. S., Corcoran, E. E., Hattangadi, N. A., Zhang, J. V., Gere, S. A., and Hellinga, H. W. (1997) The rational design of allosteric interactions in a monomeric protein and its applications to the construction of biosensors, *Proc. Natl. Acad. Sci. USA* 94:4366–4371.
17. Marvin, J. S. and Hellinga, H. W. (1998) Engineering biosensors by introducing fluorescent allosteric signal transducers: Construction of a novel glucose sensor, *J. Am. Chem. Soc.* 120:7–11.
18. Careaga, C. L., Sutherland, J., Sabeti, J., and Falke, J. J. (1995) Large amplitude twisting motions of an interdomain hinge: A disulfide trapping study of the glucose-galactose binding protein, *Biochem.* 34:3048–3055.
19. Boos, W., Gordon, A. S., Hall, R. E. and Price, H. D. (1972) Transport properties of the galactose-binding protein of *Escherichia coli*, *J. Biol. Chem.* 247(3):917–924.
20. Boos, W. (1972) Structurally defective galactose-binding protein isolated from a mutant negative in the methyl galactoside transport system of *Escherichia coli. J. Biol. Chem.* 247(17):5414–5424.
21. Strange, P. G. and Koshland, D. G. (1976) Receptor interactions in a signalling system: Competition between ribose receptor and galactose receptor in the chemotaxis response. *Proc. Nat'l Acad. Sci. USA* 73(3):762–766.
22. Zukin, R. S., Strange, P. G., Heavey L. R. and Koshland, D. E. (1977) Properties of the galactose binding protein of *Salmonella typimurium* and *Escherichia coli, Biochemistry* 16(3):381–386.
23. Tamada, J. A., Bohannon, N. J. V., and Potts, R. O. (1995) Measurement of glucose in diabetic subjects using noninvasive transdermal extraction, *Nature Med.* 1(11):1198–1201.
24. Jacques, S. L., McAuliffe, D. J., Blank, l. H., Parrish, J. A. (1987) Controlled removal of human stratum corneum by pulsed laser, *J. Investig. Dermatol.* 88:88–93.
25. Ito, N., Kayashima, S., Kimura, J., Kuriyama, T., Arai, T., Kikuchi, M., and Nagata, N. (1994) Development of a transcutaneous blood constituent monitoring method using a suction effusion fluid collection technique and an ion-sensitive field-effect transistor glucose sensor, *Biosensors* 32:242–246.
26. Berndt, K. W., Gryczynski, l., and Lakowicz, J. R. (1990) Phase-modulation fluorometry using a frequency-doubled pulsed laser diode light source, *Rev. Sci. Instrum.* 61:1816–1820.
27. Sipior, J., Carter, G. M., Lakowicz, J. R., and Rao, G. (1997) Blue light-emitting diode demonstrated as an ultraviolet excitation source for nanosecond phase modulation fluorescence lifetime measurements, *Rev. Sci. Instrum.* 68(7):2666–2670.
28. Berndt, K. W., and Lakowicz, J. R. (1992) Electroluminescent lamp-based fluorometer and oxygen sensor, *Anal. Biochem.* 201:319–325.
29. Neu, H. C., and Heppel, L. A. (1965) The release of enzymes from *Escherichia coli* by osmotic shock and during the formation of spheroplasts. *J. Biol. Chem.* 240(9):3685–3691.
30. Boos, W., and Gordon, A. S. (1971) Transport properties of the galactose binding protein of *Escherichia coli. J. Biol. Chem.* 246(3):621–628.
31. Slavik, I. (1982) Aniline naphthalene sulfonate as a probe of membrane composition and function, *Biochim. Biophys. Acta.* 694:1–25.
32. Lakowicz, J. R., Castellano, F. N., Dattelbaum, J. D., Tolosa, L., Rao, G. and Gryczynski, I., Low Frequency Modulation Sensors Using Nanosecond Fluorophores, *Anal. Chem.* 70:5115–5121 (1998).
33. Lakowicz, J. R., and Maliwal, B. P. (1985) Construction and performance of a variable-frequency phase-modulation fluorometer, *Biophys. Chem.* 21:61–78.
34. Feddersen, B. A., Piston, D. W., and Gratton, E. (1989) Digital parallel acquisition in frequency-domain fluorimetry, *Rev. Sci. Instrum.* 60(9):2929–2936.
35. Castellano, F. N., and Lakowicz, J. R. (1998) A water-soluble luminescence oxygen sensor, *Photochem. Photobiol.* 67(2):179–183.
36. Sipior, J., Carter, G. M., Lakowicz, J. R., and Rao, G. (1996) Single quantum well light emitting diodes demonstrated as excitation sources for nanosecond phase-modulation fluorescence lifetime measurements, *Rev. Sci. Instrum.* 67(11):3795–3798.
37. Harms, P., Sipior, J., Ram, N., Carter, G. M., and Rao, G. (1999) Low cost phase modulation measurements of nanosecond fluorescece lifetimes using a lock-in amplifier. *Rev.Sci.Instrum.* 70:1535–1539.
38. Scholle, et al., Sequence of the mglB gene from *Escherichia coli* K12: comparison of wild-type and mutant Galactose chemoreceptors. *Mol.Gen.Genet.* 208(1–2):247–53, 1987

What is claimed is:

1. A method for determining the presence or concentration of an analyte in a sample, comprising the steps of:
    a) providing a protein sensing molecule that is capable of binding said analyte in said sample, said molecule having a detectable quality that changes in a concentration-dependent manner when said molecule is bound to said analyte;
    b) exposing said sensing molecule to said sample; and
    c) measuring any change in said detectable quality to thereby determine the presence or concentration of said analyte in said sample.

2. The method of claim 1, wherein the analyte is a sugar.

3. The method of claim 2, wherein the sugar is selected from the group consisting of glucose, lactose, galactose, sucrose and maltose.

4. The method of claim 3, wherein the sugar is glucose.

5. The method of claim 1, wherein the sensing molecule is selected from the group consisting of glucose/galactose binding protein, hexokinase and glucokinase.

6. The method of claim 4, wherein the sensing molecule is a glucose/galactose binding protein.

7. The method of claim 1, wherein the sensing molecule is a modified protein selected from the group consisting of modified glucose/galactose binding protein, modified hexokinase and modified glucokinase.

8. The method of claim 7, wherein the protein is modified by substituting at least one cysteine residue therein.

9. The method of claim 8, wherein the protein is modified by substituting two cysteine residues therein.

10. The method of claim 8, wherein the protein is a modified glucose/galactose binding protein that contains a cysteine residue at one or both of positions 26 and 182.

11. The method of claim 1, wherein the sensing molecule is a fusion protein which contains at least one detectable segment.

12. The method of claim 11, wherein the sensing molecule is a fusion protein which contains two detectable segments.

13. The method of claim 11, wherein the detectable segment comprises green fluorescent protein or fluorescent variants thereof.

14. The method of claim 12, wherein one detectable segment comprises green fluorescent protein or fluorescent variants thereof, and the other detectable segment comprises blue fluorescent protein or fluorescent variants thereof.

15. The method of claim 1, wherein the detectable quality results from at least one detectable label associated with the sensing molecule.

16. The method of claim 15, wherein the label is a fluorescent label.

17. The method of claim 15, wherein the label is a non-fluorescent energy transfer acceptor.

18. The method of claim 1, wherein the sensing molecule comprises an energy donor moiety and an energy acceptor moiety, each bound to the sensing molecule and spaced such that there is a detectable signal change when the sensing molecule is bound to the analyte.

19. The method of claim 13, wherein the sensing molecule further comprises an energy donor moiety or an energy acceptor moiety.

20. The method of claim 1, wherein the detectable quality is a detectable spectral change.

21. The method of claim 20, wherein the detectable spectral change is a change in fluorescent decay time.

22. The method of claim 20, wherein the detectable spectral change is a change in fluorescent intensity.

23. The method of claim 20, wherein the detectable spectral change is a change in fluorescent anisotropy or polarization.

24. The method of claim 20, wherein the detectable spectral change is spectral shift of the emission spectrum.

25. The method of claim 21, wherein the change in fluorescent decay time is determined by time domain measurement.

26. The method of claim 21, wherein the change in fluorescent decay time is determined by frequency domain measurement.

27. The method of claim 20, wherein the detectable spectral change is a change in time-resolved anisotropy decay.

28. The method of claim 27, wherein the change in time-resolved anisotropy decay is determined by time domain measurement.

29. The method of claim 27, wherein the change in time-resolved anisotropy decay is determined by frequency domain measurement.

30. A sensor for determining the presence or concentration of an analyte in a sample, which comprises:
   a) a protein sensing molecule that is capable of binding to the analyte in said sample, said molecule having a detectable quality that changes in a concentration-dependent manner when said molecule is bound to the analyte;
   b) a radiation source which is capable of causing said sensing molecule to emit said detectable quality; and
   c) means for detecting changes in said detectable quality in response to said analyte binding.

31. The sensor of claim 30, wherein the analyte is a sugar.

32. The sensor of claim 31, wherein the sugar is selected from the group consisting of glucose, lactose, galactose, sucrose and maltose.

33. The sensor of claim 32, wherein the sugar is glucose.

34. The sensor of claim 30, wherein the sensing molecule is selected from the group consisting of glucose/galactose binding protein, hexokinase and glucokinase.

35. The sensor of claim 33, wherein the sensing molecule is a glucose/galactose binding protein.

36. The sensor of claim 30, wherein the sensing molecule is a modified protein selected from the group consisting of modified glucose/galactose binding protein, modified hexokinase and modified glucokinase.

37. The sensor of claim 36, wherein the protein is modified by substituting at least one cysteine residue therein.

38. The sensor of claim 37, wherein the protein is modified by substituting two cysteine residues therein.

39. The sensor of claim 37, wherein the protein is a modified glucose/galactose binding protein that contains a cysteine residue at one or both of positions 26 and 182.

40. The sensor of claim 30, wherein the sensing molecule is a fusion protein which contains at least one detectable segment.

41. The sensor of claim 40, wherein the sensing molecule is a fusion protein which contains two detectable segments.

42. The sensor of claim 40, wherein the detectable segment comprises green fluorescent protein or fluorescent variants thereof.

43. The sensor of claim 41, wherein one detectable segment comprises green fluorescent protein or fluorescent variants thereof, and the other detectable segment comprises blue fluorescent protein or fluorescent variants thereof.

44. The sensor of claim 30, wherein the detectable quality results from at least one detectable label associated with the sensing molecule.

45. The sensor of claim 44, wherein the label is a fluorescent label.

46. The sensor of claim 44, wherein the label is a non-fluorescent energy transfer acceptor.

47. The sensor of claim 30, wherein the sensing molecule comprises an energy donor moiety and an energy acceptor moiety, each bound to the sensing molecule and spaced such that there is a detectable signal change when the sensing molecule is bound to the analyte.

48. The sensor of claim 42, wherein the sensing molecule further comprises an energy donor moiety or an energy acceptor moiety.

49. The sensor of claim 30, wherein the detectable quality is a detectable spectral change.

50. The sensor of claim 49, wherein the detectable spectral change is a change in fluorescent decay time.

51. The sensor of claim 49, wherein the detectable spectral change is a change in fluorescent intensity.

52. The sensor of claim 49, wherein the detectable spectral change is a change in fluorescent anisotropy or polarization.

53. The sensor of claim 49, wherein the detectable spectral change is spectral shift of the emission spectrum.

54. The sensor of claim 50, wherein the change in fluorescent decay time is determined by time domain measurement.

55. The sensor of claim 50, wherein the change in fluorescent decay time is determined by frequency domain measurement.

56. The sensor of claim 49, wherein the detectable spectral change is a change in time-resolved anisotropy decay.

57. The sensor of claim 56, wherein the change in time-resolved anisotropy decay is determined by time domain measurement.

58. The sensor of claim 56, wherein the change in time-resolved anisotropy decay is determined by frequency domain measurement.

* * * * *